United States Patent
Freeman

(10) Patent No.: US 11,653,605 B2
(45) Date of Patent: May 23, 2023

(54) HYBRID CARROT VARIETY NUN 89733 CAC

(71) Applicant: NUNHEMS B.V., Nunhem (NL)

(72) Inventor: Roger E. Freeman, Brooks, OR (US)

(73) Assignee: NUNHEMS B.V., Nunhem (NL)

( * ) Notice: Subject to any disclaimer, the term of this patent is extended or adjusted under 35 U.S.C. 154(b) by 19 days.

(21) Appl. No.: 17/227,046

(22) Filed: Apr. 9, 2021

(65) Prior Publication Data

US 2021/0227765 A1    Jul. 29, 2021

Related U.S. Application Data

(60) Provisional application No. 63/008,345, filed on Apr. 10, 2020.

(51) Int. Cl.
| | |
|---|---|
| *A01H 6/06* | (2018.01) |
| *A01H 5/06* | (2018.01) |
| *A01H 5/10* | (2018.01) |
| *A01H 5/12* | (2018.01) |

(52) U.S. Cl.
CPC .............. *A01H 6/068* (2018.05); *A01H 5/06* (2013.01); *A01H 5/10* (2013.01); *A01H 5/12* (2013.01)

(58) Field of Classification Search
CPC ...................................... A01H 6/068
See application file for complete search history.

(56) References Cited

U.S. PATENT DOCUMENTS

| | | | | |
|---|---|---|---|---|
| 9,012,724 B2* | 4/2015 | Freeman | ................ | A01H 6/068 800/267 |
| 2015/0126380 A1 | 5/2015 | Van Dun | | |
| 2015/0245570 A1 | 9/2015 | Vogelaar et al. | | |

OTHER PUBLICATIONS

"Calibration Book—Carrot", Naktuinbouw Calibration Book, *Daucus carota* L.—Carrot, Version 1, Dec. 2010, 52 pages.
"General introduction to the examination of Distinctness, Uniformity and Stability and the development of harmonized descriptions of new varieties of plants", UPOV, International Union for the Protection of New Varieties of Plants, Geneva. TG/1/3, Apr. 19, 2002, 26 pages.
"Carrot—UPOV Code(s): DAUCU_CAR, *Daucus carota* L.", Guidelines for the conduct of tests for Distinctness, Uniformity and Stability, UPOV, International Union for the Protection of New Varieties of Plants, Geneva, TG/49/8, Mar. 25, 2015, 32 pages.
"Objective Description of Variety—Carrot (*Daucus carota*)", US Department of Agriculture, Agricultural Marketing Service, Science and Technology, Plant Variety Protection Office, USDA, Exhibit C, Jun. 2015, 4 pages.
Arnholdt-Schmitt, et al., "Physiological aspects of genome variability in tissue culture. I. Growth phase-dependent differential DNA methylation of the carrot genome (*Daucus carota* L.) during primary culture", Theoretical and Applied Genetics, vol. 91, Issue 5, Oct. 1995, pp. 809-815.
Jhang, et al., "Efficiency of different marker systems for molecular characterization of subtropical carrot germplasm", The Journal of Agricultural Science, vol. 148, Issue 2, 2010, pp. 171-181.
Larkin, et al., "Somaclonal variation—a novel source of variability from cell cultures for plant improvement", Theoretical and Applied Genetics, vol. 60, Issue 4, Feb. 21, 2006, pp. 197-214.
Martin, et al., "Identification of markers linked to agronomic traits in globe artichoke", Australian Journal of Crop Science, vol. 1, Issue 2, 2008, pp. 43-46.
Needleman, et al., "A general method applicable to the search for similarities in the amino acid sequence of two proteins", Journal of Molecular Biology, vol. 48, Issue 3, Mar. 28, 1970, pp. 443-453.
Nikolova, et al., "Diploidization of cucumber (*Cucumis sativus* L.) haploids by colchicine treatment", Acta Societas Botanicorum Poloniae, vol. 65, Issue 3-4, 1996, pp. 311-317.
Nuñez, et al., "Carrot Production in California,", University of California, Division of Agriculture and Natural Resources, Publication 7226, 1997, 5 pages.
Rice, et al., "EMBOSS: The European Molecular Biology Open Software Suite", Trends in Genetics, vol. 16, Issue 6, Jun. 1, 2000, pp. 276-277.
Robert W. Allard, "Overview of Plant Breeding", Principles of Plant Breeding, Second Edition, May 1999, pp. 34-67.
Shim, et al., "Genetic structure in cultivated and wild carrots (*Daucus carota* L.) revealed by AFLP analysis", Theoretical and Applied Genetics, vol. 101, Issue 1-2, Jul. 2000, pp. 227-233.
Songstad, et al., "Genome Editing of Plants", Critical Reviews in Plant Sciences, vol. 36, Issue 1, 2017, pp. 1-23.
Stein, et al., "Some remarks on carrot breeding (*Daucus carota sativus* Horffm.)", Plant Breeding, vol. 114, Issue 1, Feb. 1995, pp. 1-11.
Vos, et al., "AFLP: a new technique for DNA fingerprinting", Nucleic Acids Research, vol. 23, Issue 21, Nov. 11, 1995, pp. 4407-4414.
Wijnker, et al., "Hybrid recreation by reverse breeding in Arabidopsis thaliana", Nature Protocols, vol. 9, Issue 4, Mar. 6, 2014, pp. 761-772.

* cited by examiner

*Primary Examiner* — David H Kruse

(74) *Attorney, Agent, or Firm* — ArentFox Schiff LLP

(57) ABSTRACT

A hybrid carrot variety NUN 89733 CAC as well as seeds and plants and roots thereof is disclosed. NUN 89733 CAC is a purple imperator-shaped carrot variety for the fresh market.

27 Claims, 3 Drawing Sheets

US 11,653,605 B2

HYBRID CARROT VARIETY NUN 89733 CAC

CROSS-REFERENCE TO RELATED APPLICATION

This application claims priority to U.S. Provisional application No. 63/008,345, filed on Apr. 10, 2020, which is hereby incorporated by reference in its entirety.

FIELD OF THE DISCLOSURE

The present disclosure relates to the field of plant breeding, more specifically to carrot variety NUN 89733 CAC. The disclosure further relates to vegetative reproductions of carrot variety NUN 89733 CAC, methods for tissue culture of carrot variety NUN 89733 CAC and regenerating a plant from such a tissue culture, and also to phenotypic variants of carrot variety NUN 89733 CAC. The disclosure also relates to progeny of carrot variety NUN 89733 CAC and the hybrid varieties obtained by crossing carrot variety NUN 89733 CAC as a parent line with plants of other varieties or parent lines.

BACKGROUND OF THE DISCLOSURE

The goal of vegetable breeding is to combine various desirable traits in a single variety or hybrid. Such desirable traits may include greater yield, resistance to diseases, insects or other pests, tolerance to heat and drought, better agronomic quality, higher nutritional value, enhanced growth rate and improved root properties.

Breeding techniques take advantage of a plant's method of pollination. There are two general methods of pollination: a plant self-pollinates if pollen from one flower is transferred to the same or another flower of the same genotype. A plant cross-pollinates if pollen comes to it from a flower of a different genotype. Plants that have been self-pollinated and selected for (uniform) type over many generations become homozygous at almost all gene loci and produce a uniform population of true breeding progeny of homozygous plants. A cross between two such homozygous plants of different lines produces a uniform population of hybrid plants that are heterozygous for many gene loci. The extent of heterozygosity in the hybrid is a function of the genetic distance between the parents. Conversely, a cross of two plants each heterozygous at a number of loci produces a segregating population of hybrid plants that differ genetically and are not uniform. The resulting non-uniformity makes performance unpredictable.

The development of uniform varieties requires the development of homozygous inbred plants, the crossing of these inbred plants to make hybrids, optionally three-way hybrids, and the evaluation of the hybrids resulting from the crosses. Pedigree breeding and recurrent selection are examples of breeding methods that have been used to develop inbred plants from breeding populations. Those breeding methods combine the genetic backgrounds from two or more plants or various other broad-based sources into breeding pools from which new lines are developed by selfing and selection of desired phenotypes. The new plants are evaluated to determine which have commercial potential.

One crop species which has been subject to such breeding programs and is of particular value is the carrot. Carrot (*Daucus carota* subsp. *sativus*), is a biennial plant that grows a rosette of leaves in the spring and summer, while building up the stout taproot, which stores large amounts of sugars for the plant to flower in the second year. The flowering stem grows several decimeters (e.g., 60-200 cm) tall, with an umbel of white flowers that produce a fruit called a mericarp.

Carrot is grown as a root vegetable, usually orange in color, though purple, red, white, cream, and yellow varieties exist. It has a crisp texture when fresh. The most commonly eaten part of a carrot is the root, although the greens are edible as well. It is a domesticated form of the wild carrot *Daucus carota*, native to Europe and Southwestern Asia. The domestic carrot has been selectively bred for its greatly enlarged and more palatable, less woody-textured edible taproot. Carrots are primarily consumed fresh as snack food, raw vegetable or as salad ingredient. Carrots are also popular as cooking vegetable and can be frozen and juiced.

United States is one of the largest carrot producers in the world. Between 1994 and 2018, an average production of 1.6 million tons of carrots were produced in the United States (see, e.g., world-wide web at fao.org under statistics). Carrots are grown year-round in the United States with the highest volume coming from California from December to August.

While breeding efforts to date have provided a number of useful carrot varieties with beneficial traits, there remains a great need in the art for new varieties with further improved traits. Such plants would benefit farmers and consumers alike by improving crop yields and/or quality. Some breeding objectives include varying the color, size and shape of the root, flavor or taste, nutritional quality, post-harvest quality, disease or pest resistance, yield, suitability to various climatic circumstances, and storage properties.

SUMMARY OF THE VARIOUS ASPECTS OF THE DISCLOSURE

The disclosure provides for carrot variety NUN 89733 CAC, products thereof, and methods of using the same. NUN 89733 CAC is a purple imperator-shaped carrot variety for the fresh market and is suitable for the open field.

In another aspect, the plant of carrot variety NUN 89733 CAC, or part thereof, or progeny thereof has 21, 22, or more or all of the distinguishing characteristics as shown in Table 3: 1) semi-erect plant top habit; 2) shorter plant top; 3) medium leaf blade division; 4) shorter blade without petiole; 4) without petiole pubescence; 5) shorter leaf including petiole; 6) shorter petiole; 7) smaller core (xylem) thickness; 8) shorter root length minus taproot; 9) longer taproot; 10) smaller root shoulder; 11) smaller root at midpoint; 12) very smooth surface; 13) absent or very weak root ridging of surface; 14) absent or very small extent of green coloration in longitudinal section; 15) lighter root weight; 16) darker purple color of below ground exterior shoulder; 17) darker purple color of below ground exterior skin color; 18) lighter yellow color of cross-section xylem (core); 19) light purple color of cross-section phloem (cortex); 20) medium intensity of core color; 21) light intensity of cortex color; and 22) dark intensity of external color, when determined at 5% significance level for numerical characteristics and determined by type or degree for non-numerical characteristics, when grown under the same environmental conditions.

The disclosure also provides for a carrot plant or part thereof having all of the physiological and morphological characteristics of carrot variety NUN 89733 CAC when grown under the same environmental conditions.

In another aspect, the disclosure for a progeny of carrot variety NUN 89733 CAC. In a further aspect, the plant or progeny retains all or all but one, two, or three of the "distinguishing characteristics" of carrot variety NUN 89733 CAC, or all but one, two, or three of the "physiological and morphological characteristics" of carrot variety NUN 89733 CAC and methods of producing that plant or progeny.

In another aspect, the plant or such progeny has all or all but one, two, or three of the physiological and morphological characteristics of carrot variety NUN 89733 CAC when measured under the same environmental conditions and e.g., evaluated at significance levels of 1%, 5%, or 10% significance (which can also be expressed as p-value) for quantitative characteristics and determined by type or degree for non-quantitative characteristics, wherein a representative sample of seed of carrot variety NUN 89733 CAC has been deposited under Accession Number NCIMB 44118. In another aspect, the plant or progeny has all or all but one, two, or three of the physiological and morphological characteristics as listed in Tables 1 and 2 of carrot variety NUN 89733 CAC, when grown under the same environmental conditions and e.g., evaluated at significance levels of 1%, 5% or 10% significance (which can also be expressed as a p-value) for quantitative characteristics and determined by type or degree for non-quantitative characteristics.

In another aspect, the disclosure provides a seed of carrot variety NUN 89733 CAC, wherein a representative sample of said seed has been deposited under Accession Number NCIMB 44118. The disclosure also provides for a plurality of seeds of carrot variety NUN 89733 CAC. The carrot seed of carrot variety NUN 89733 CAC may be provided as an essentially homogeneous population of carrot seed. The population of seed of carrot variety NUN 89733 CAC may be particularly defined as being essentially free from other seed. The seed population may be grown into plants to provide an essentially homogeneous population of carrot plants as described herein.

The disclosure also provides a plant grown from a seed of carrot variety NUN 89733 CAC and a plant part thereof.

The disclosure also provides a carrot root produced on a plant grown from a seed of carrot variety NUN 89733 CAC.

The disclosure furthermore provides a seed growing or grown on a plant of carrot variety NUN 89733 CAC (i.e., produced after pollination of the flower of carrot variety NUN 89733 CAC).

In another aspect, the disclosure provides for a plant part obtained from carrot variety NUN 89733 CAC, wherein said plant part is a root, or a part of a root, a harvested root, a root tip, a taproot, a leaf, a part of a leaf, pollen, an ovule, a cell, a petiole, a shoot or a part thereof, a stem or a part thereof, a cutting, a seed, a part of a seed, seed coat or another maternal tissue which is part of a seed grown on said variety, a hypocotyl, a cotyledon, a pistil, an anther, and a flower or a part thereof. Roots are particularly important plant parts. In another aspect, the plant part obtained from carrot variety NUN 89733 CAC is a cell, optionally a cell in a cell or tissue culture. That cell may be grown into a plant of carrot variety NUN 89733 CAC.

In another aspect, the disclosure provides for a hybrid carrot variety NUN 89733 CAC.

The disclosure also provides a cell culture of carrot variety NUN 89733 CAC and a plant regenerated from carrot variety NUN 89733 CAC, wherein the plant has all or all but one, two, or three of the morphological and physiological characteristics of carrot variety NUN 89733 CAC, when grown under the same environmental conditions, as well as methods for culturing and regenerating carrot variety NUN 89733 CAC. Alternatively, a regenerated plant may have one characteristic that is different from carrot variety NUN 89733 CAC.

The disclosure further provides a vegetatively propagated plant of variety NUN 89733 CAC or part thereof, wherein the plant or part thereof have all or all but one, two, or three of the morphological and physiological characteristics of carrot variety NUN 89733 CAC, when grown under the same environmental conditions as well as methods for vegetatively propagating carrot variety NUN 89733 CAC.

In another aspect, the disclosure provides a method of producing a carrot plant comprising crossing carrot variety NUN 89733 CAC with itself or another carrot variety and selecting a progeny carrot variety from said crossing or selfing.

The disclosure also provides a method of producing a carrot plant derived from carrot variety NUN 89733 CAC.

In a further aspect, the disclosure provides a method of producing hybrid carrot seed comprising crossing a first parent carrot plant with a second parent carrot plant and harvesting the resultant hybrid carrot seed, wherein said first parent carrot plant or second parent carrot plant is carrot variety NUN 89733 CAC. Also provided is a hybrid carrot seed produced from crossing a first parent carrot plant with a second parent carrot plant and harvesting the resultant seed, wherein first said first parent carrot plant or second parent carrot plant is carrot variety NUN 89733 CAC. Moreover, the hybrid carrot plant grown from the hybrid carrot seed is provided.

In another aspect, the disclosure provides a method of introducing a single locus conversion into the plant of variety NUN 89733 CAC, wherein a representative sample of seed of seed of said carrot variety has been deposited under Accession Number NCIMB 44118, wherein the plant otherwise comprises the single locus conversion and has all of the morphological and physiological characteristics of carrot variety NUN 89733 CAC.

In yet another aspect, the disclosure provides a method of introducing a desired trait into carrot variety NUN 89733 CAC, said method comprises transforming the plant of variety NUN 89733 CAC, with a transgene that confers the desired trait, wherein the transformed plant otherwise comprises the desired trait and has all of the morphological and physiological characteristics of carrot variety NUN 89733 CAC.

The disclosure also provides a method of producing a modified carrot variety with a desired trait, wherein the method comprises mutating a carrot plant or plant part of variety NUN 89733 CAC, wherein a representative sample of seed of said carrot variety has been deposited under Accession Number NCIMB 44118, and wherein the mutated plant otherwise comprises the desired trait and has all of the morphological and physiological characteristics of carrot variety NUN 89733 CAC.

In one aspect, the single locus conversion or desired trait is yield, size, shape, color, flavor or taste, storage properties, nutritional quality, post-harvest quality, male sterility, herbicide tolerance, insect resistance, pest resistance, disease resistance, environmental stress tolerance, modified carbohydrate metabolism, modified protein metabolism, or ripening.

In another aspect, the disclosure provides a container comprising the plant, plant part, or seed of carrot variety NUN 89733 CAC.

Also provided is a food, a feed, or a processed product comprising the plant part of carrot variety NUN 89733 CAC, wherein the plant part is a carrot root or part thereof.

DEFINITIONS

Figure 1:
FIG. 1 shows the leaf comparison of carrot variety NUN 89733 CAC and the Reference Variety.
Figure 2:
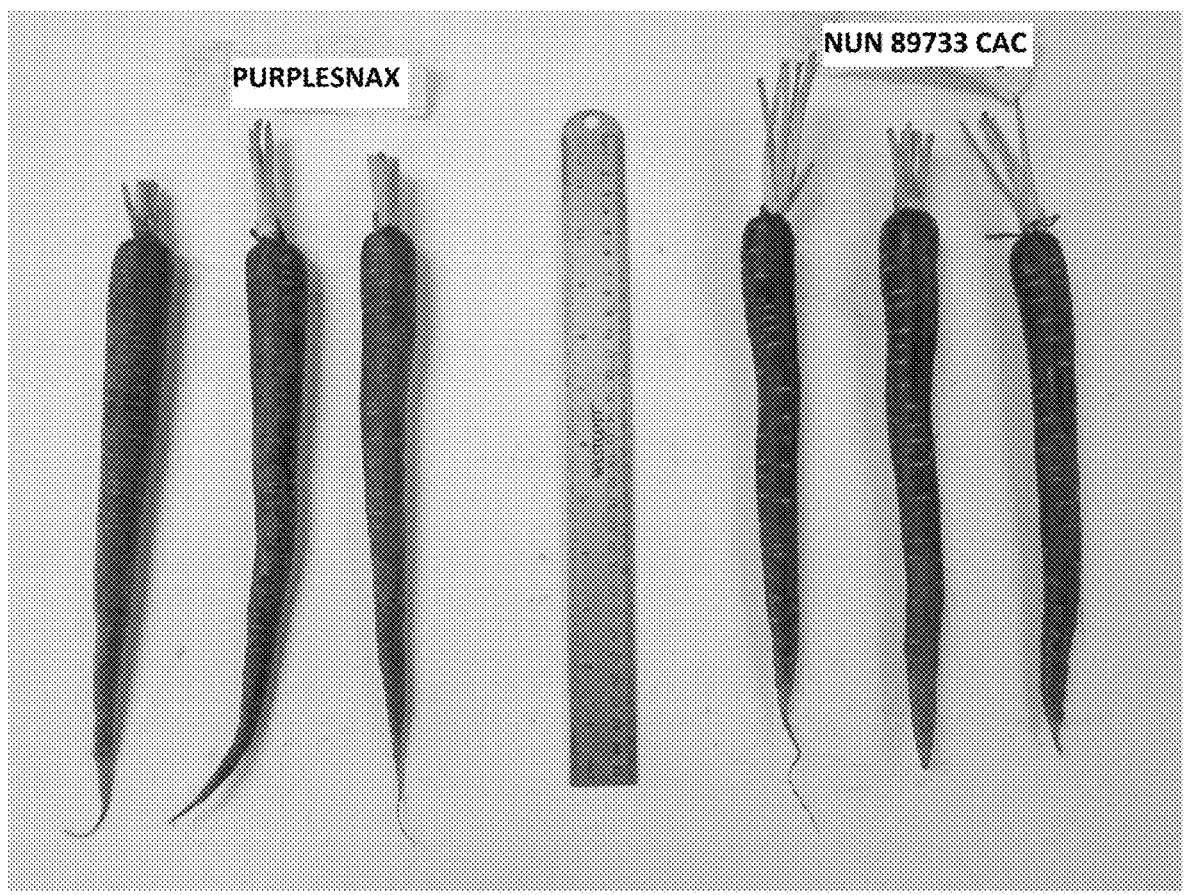
FIG. 2 shows the root comparison at market maturity of carrot variety NUN 89733 CAC and the Reference Variety.
Figure 3:
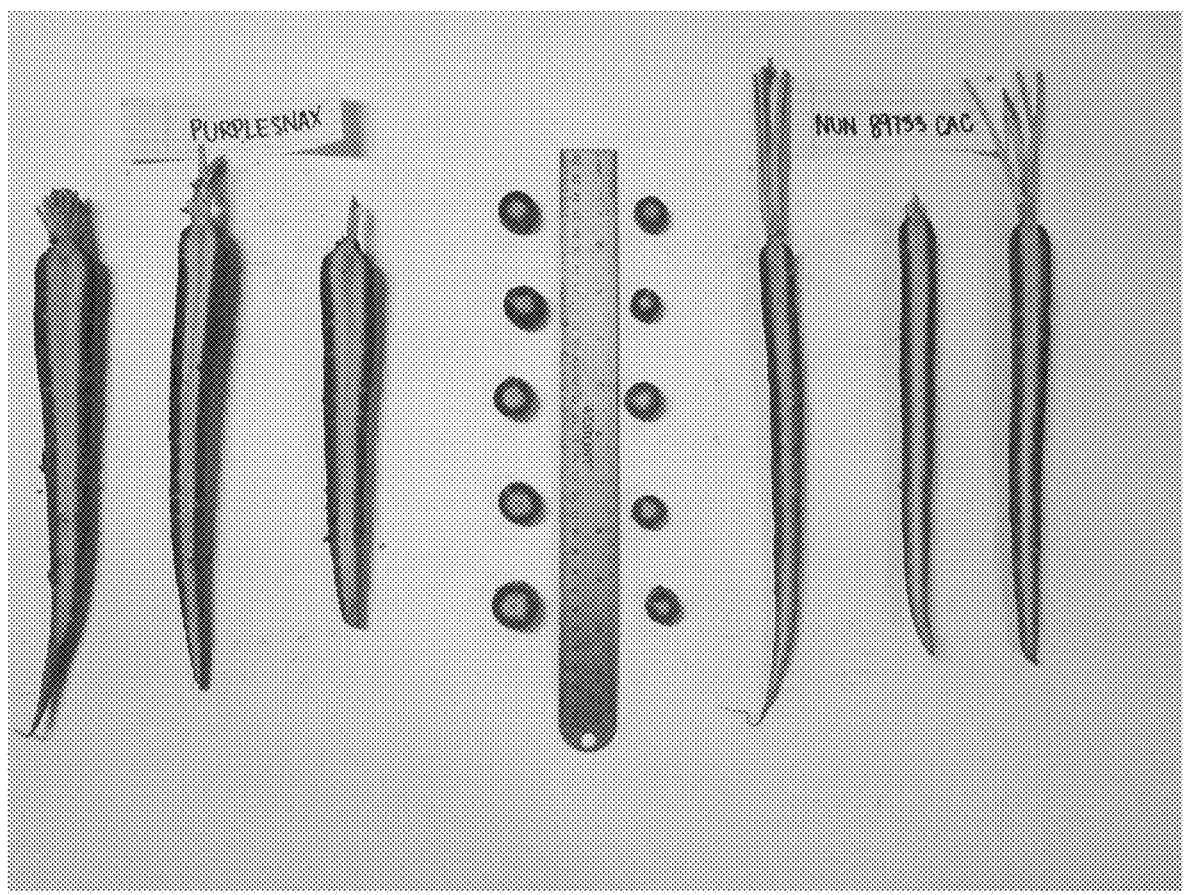
FIG. 3 shows the root cross-section comparison at market maturity of carrot variety NUN 89733 CAC and the Reference Variety.

"Carrot" refers herein to plants of the species *Daucus carota*. The most commonly eaten part of a carrot is the root.

"Cultivated carrot" refers to plants of *Daucus carota* (e.g., varieties, breeding lines, or cultivars of the species *D. carota*, as well as crossbreds thereof, or crossbreds with other *Daucus carota* species), cultivated by humans and having good agronomic characteristics.

The terms "carrot plant designated NUN 89733 CAC," "NUN 89733 CAC," "NUN 89733," "NUN 89733 F1," "89733 CAC," or "carrot 89733" are used interchangeably herein and refer to a carrot plant of variety NUN 89733 CAC, representative sample of seed of said carrot variety has been deposited under Accession Number NCIMB 44118.

A "seed of NUN 89733 CAC" refers to a carrot seed which can be grown into a plant of carrot variety NUN 89733 CAC, wherein a representative sample of viable seed of carrot variety NUN 89733 CAC has been deposited under Accession Number NCIMB 44118. A seed can be in any stage of maturity, for example, a mature, viable seed, or an immature, non-viable seed. A seed comprises an embryo and maternal tissues.

An "embryo of NUN 89733 CAC" refers to an "F1 hybrid embryo" as present in a seed of carrot variety NUN 89733 CAC, a representative sample of said seed of carrot variety NUN 89733 CAC has been deposited under Accession Number NCIMB 44118.

A "seed grown on NUN 89733 CAC" refers to a seed grown on a mature plant of carrot variety NUN 89733 CAC. The "seed grown on NUN 89733 CAC" contains tissues and DNA of the maternal parent, carrot variety NUN 89733 CAC. When said seed is planted, it grows into a first generation progeny plant of carrot variety NUN 89733 CAC.

"Plant" includes the whole plant or any parts or derivatives thereof, having the same genetic makeup as the plant from which it is obtained.

"Plant part" includes any part of a plant, such as a plant organ (e.g., harvested or non-harvested roots), a plant cell, a plant protoplast, a plant cell tissue culture or a tissue culture from which a whole plant can be regenerated, a plant cell that is intact in a plant, a clone, a micropropagation, plant callus, a plant cell clump, a plant transplant, a vegetative propagation, a seedling, or a part of a plant (e.g., harvested tissues or organs), such as a root, or a part of a root, a harvested root, a root tip, a fruit, a harvested fruit, a part of a fruit, a leaf, a part of a leaf, pollen, an ovule, an embryo, a petiole, a shoot or a part thereof, a stem or a part thereof, a cutting, a seed, a part of a seed, seed coat or another maternal tissue, hypocotyl, cotyledon, a pistil, an anther, and a flower or parts of any of these and the like. Seed can be mature or immature. Pollen or ovules may be viable or non-viable. Also, any developmental stage is included, such as seedlings, cuttings prior or after rooting, mature plants or leaves. Alternatively, a plant part may also include a plant seed which comprises maternal tissues of carrot variety NUN 89733 CAC and an embryo having one or two sets of chromosomes derived from the parent plant, e.g., from carrot variety NUN 89733 CAC. Such an embryo comprises two sets of chromosomes derived from carrot variety NUN 89733 CAC, if it produced from self-pollination of said variety, while an embryo derived from cross-fertilization of carrot variety NUN 89733 CAC will comprise only one set of chromosomes from carrot variety NUN 89733 CAC, and the other set of chromosomes from the other parent.

An "essentially homogeneous population of carrot seed" is a population of seeds where at least 97%, 98%, or 99% or more of the total population of seed are seeds of carrot variety NUN 89733 CAC.

An "essentially homogeneous population of carrot plants" is a population of plants where at least 97%, 98%, 99% or more of the total population of plants are plants of carrot variety NUN 89733 CAC.

The phrase "essentially free from other seed" refers to a population of seed where less than 3%, 2%, 1% or less of the total population of seed is seed that is not a carrot seed or, in another aspect, less than 3%, 2%, 1% or less of the total population of seed is seed that is not a seed of carrot variety NUN 89733 CAC.

"Uniform throughout the root" refers to a characteristic such as color being identical throughout the entire plant part (e.g., throughout the root when it is cut in half).

"Harvest maturity" refers to the stage at which a carrot root is ready for harvest or the optimal time to harvest the root for the market, for processing or for consumption. In one aspect, harvest maturity is the stage suitable for producing baby carrots.

"Harvested plant material" refers herein to plant parts (e.g., roots removed from the soil in which they were growing) which have been collected for further storage and/or further use.

"Yield" means the total weight of all carrot roots harvested per hectare of a particular line or variety. It is understood that "yield" expressed as weight of all carrots harvested per hectare can be obtained by multiplying the number of plants per hectare times the "yield per plant".

"Marketable yield" means the total weight of all marketable carrot roots, especially roots that are not split, damaged or diseased, harvested per hectare of a particular line or variety.

"Refractometer % of soluble solids" refers to the percentage of soluble solids in juice of pureed roots (mainly sugar), as defined by the USDA. It is also expressed as ° Brix and indicates sweetness in the roots of carrot. Brix can be measured using a Brix meter (also known as Refractometer).

"USDA descriptors" are the plant variety descriptors described for carrot in the "Objective description of Variety—Carrot (*Daucus carota*)," as published by U.S. Department of Agriculture, Agricultural Marketing Service, Science and Technology, Plant Variety Protection Office, Beltsville, Md. 20705 and which can be downloaded from the world-wide web at ams.usda.gov/under services/plant-variety-protection/pvpo-c-forms under carrot. "Non-USDA descriptors" are other descriptors suitable for describing carrot.

"UPOV descriptors" are the plant variety descriptors described for carrot in the "Guidelines for the Conduct of Tests for Distinctness, Uniformity and Stability, TG/49/8 (Geneva 2007, last updated in 2015-03-25), as published by UPOV (International Union for the Protection of New Varieties and Plants) and which can be downloaded from the world wide web at upov.int/under edocs/tgdocs/en/tg049.pdf and is herein incorporated by reference in its entirety. Likewise, "UPOV methods" to determine specific parameters for the characterization of carrot are described at upov.int.

"Calibration book *Daucus carota* L." refers to the calibration book for carrot which provides guidance for describing a carrot variety, as published by Naktuinbow (Netherlands), December 2010 and based on the UPOV Guideline TG/13.

"RHS" or "RHS color" refers to the Royal Horticultural Society (UK), which publishes an official botanical color chart quantitatively identifying colors according to a defined numbering system. The chart may be purchased from Royal Horticulture Society Enterprise Ltd RHS Garden; Wisley, Woking; Surrey GU236QB, UK, e.g., the RHS color chart: 2007.

"Reference Variety" for carrot NUN 89733 CAC refers herein to variety NUN 89731 CAC, a commercial variety from Nunhems B.V. with commercial name, PurpleSnax, which has been planted in a trial together with carrot variety NUN 89733 CAC. The characteristics of carrot variety NUN 89733 CAC are compared to the characteristics of the Reference Variety as shown in Tables 1 and 2. The distinguishing characteristics between carrot variety NUN 89733 CAC and the Reference Variety are shown in Table 3.

A plant having "all the physiological and morphological characteristics" of a referred-to-plant means a plant showing the physiological and morphological characteristics of the referred-to-plant when grown under the same environmental conditions, preferably in the same experiment; the referred-to-plant can be a plant from which it was derived, e.g., the progenitor plant, the parent, the recurrent parent, the plant used for tissue- or cell culture, etc. A physiological or morphological characteristic can be a numerical characteristic or a non-numerical characteristic. In one aspect, a plant has "all but one, two, or three of the physiological and morphological characteristics" of a referred-to-plant, or "all the physiological and morphological characteristics" of Tables 1 and 2 or "all or all but one, two, or three of the physiological and morphological characteristics" of Tables 1 and 2.

The physiological and/or morphological characteristics mentioned above are commonly evaluated at significance levels of 1%, 5%, or 10% if they are numerical (quantitative), or for having an identical degree (or type) if not numerical, if measured under the same environmental conditions. For example, a progeny plant or a Single Locus Converted plant or a mutated plant of carrot variety NUN 89733 CAC may have one or more (or all) of the physiological and/or morphological characteristics of said variety listed in Tables 1 and 2, as determined at the 5% significance level (i.e., p<0.05) for numerical characteristics and determined by type or degree for non-numerical characteristics, when grown under the same environmental conditions.

"Distinguishing characteristics" or "distinguishing morphological and/or physiological characteristics" refers herein to the characteristics which distinguish the new variety from the other carrot varieties, such as the Reference Variety (i.e., are different), when grown under the same environmental conditions. The distinguishing characteristics between carrot variety NUN 89733 CAC and the Reference Variety are described in Table 3. When comparing carrot variety NUN 89733 CAC to other varieties, the distinguishing characteristics may be different. In one aspect, the distinguishing characteristics may therefore include at least one, two, three or more (or all) of the characteristics listed in Tables 1 and 2. All numerical distinguishing characteristics are statistically significantly different at p<0.05 between carrot variety NUN 89733 CAC and the other variety (e.g., Reference Variety). All non-numerical distinguishing characteristics are different (in type or degree) between carrot variety NUN 89733 CAC and the other variety (e.g., Reference Variety).

Carrot variety NUN 89733 CAC has the following distinguishing characteristics when compared to the Reference Variety as shown in Table 3: 1) semi-erect plant top habit; 2) shorter plant top; 3) medium leaf blade division; 4) shorter blade without petiole; 4) without petiole pubescence; 5) shorter leaf including petiole; 6) shorter petiole; 7) smaller core (xylem) thickness; 8) shorter root length minus taproot; 9) longer taproot; 10) smaller root shoulder; 11) smaller root at midpoint; 12) very smooth surface; 13) absent or very weak root ridging of surface; 14) absent or very small extent of green coloration in longitudinal section; 15) lighter root weight; 16) darker purple color of below ground exterior shoulder; 17) darker purple color of below ground exterior skin color; 18) lighter yellow color of cross-section xylem (core); 19) light purple color of cross-section phloem (cortex); 20) medium intensity of core color; 21) light intensity of cortex color; and 22) dark intensity of external color, when determined at 5% significance level for numerical characteristics and determined by type or degree for non-numerical characteristics when grown under the same environmental conditions.

Thus, a carrot plant "comprising the distinguishing characteristics of carrot variety NUN 89733 CAC" (such as a progeny plant) refers herein to a plant which does not differ from said variety when the numerical characteristics are determined at 5% significance level and determined by type or degree for non-numerical characteristics.

Similarity and differences between two different plant lines or varieties can be determined by comparing the number of morphological and/or physiological characteristics that are the same (i.e., statistically not significantly different) or that are different (i.e., statistically significantly different) between the two plant lines or varieties grown under the same environmental conditions. A numerical characteristic is considered to be "the same" when the value for a numeric characteristic is not significantly different at the 1% (p<0.01) or 5% (p<0.05) significance level, using the T-Test Paired Two Sample Means, a standard method known to the skilled person. A non-numerical characteristic is considered to be "the same" when the values have the same "degree" or "type" when scored using USDA and/or UPOV descriptors, for plants are grown under the same environmental conditions.

In one aspect, a statistical analysis of quantitative characteristics showing the degree of significance may be provided. Statistical significance is the likelihood that a relationship between two or more variables is caused by something other than chance, i.e., that the differences in the means for quantitative characteristics of carrot variety NUN 89733 CAC, and the Reference Variety are significant or due to chance. For the purpose of proving differences or distinction between carrot variety NUN 89733 CAC and the Reference Variety, a p-value of 5% (or 0.05) or lower is considered statistically significant. This means that there is only a 5% probability that the observed result could have happened just by chance or random variation.

The statistical analysis is drawn from a small sample of at least 15 plants or plants parts of carrot variety NUN 89733 CAC and the Reference Variety. Statistical points or parameters such as mean, minimum, median, maximum, and standard deviation are collected from the sample data to analyze where the average is, how varied the data set is, and whether the data is skewed. For the purpose of determining whether the result of a data set is statistically significant, a T-test Paired Sample Means is used, a statistical tool for proving significance in the means of the two groups (e.g., carrot variety NUN 89733 CAC and the Reference Variety) at 5% significance level (p-value of 5% or 0.05).

"Variety," "cultivated carrot," or "cultivar" means a plant grouping within a single botanical taxon of the lowest known rank.

A "plant line" is for example, a breeding line which can be used to develop one or more varieties. A breeding line is typically highly homozygous.

"Harvested seeds" refer to seeds harvested from a line or variety, e.g., produced after self-fertilization or cross-fertilization and collected.

"Hybrid variety" or "F1 hybrid" refers to the seeds harvested from crossing two inbred (nearly homozygous) parental lines. For example, the female parent is pollinated with pollen of the male parent to produce hybrid (F1) seeds on the female parent.

"Locus" (plural loci) refers to the specific location, place, or site of a DNA sequence on a chromosome where, for example, a gene or genetic marker is found. A locus may confer a specific trait.

"Allele" refers to one or more alternative forms of a gene locus. All of these loci relate to one trait. Sometimes, different alleles can result in different observable phenotypic traits. However, many variations at the genetic level result in little or no observable variation.

"Genotype" refers to the genetic composition of a cell or organism.

"Phenotype" refers to the detectable characteristics of a plant, cell, or organism, wherein the characteristics are the manifestation of gene expression.

The term "traditional breeding techniques" encompasses herein crossing, selfing, selection, doubled haploid production, embryo rescue, protoplast fusion, marker assisted selection, mutation breeding etc. as known to the breeder (i.e., methods other than genetic modification/transformation/transgenic methods), by which, for example, a genetically heritable trait can be transferred from one carrot line or variety to another.

"Tissue culture" or "cell culture" refers to a composition comprising isolated cells of the same or a different type or a collection of such cells organized into parts of a plant. Tissue culture of various tissues of carrot and regeneration of plants therefrom is well known and widely published (see, e.g., Arnholdt-Schmitt et al., 1995 Theor Appl Genet (1995) 91:809-815; Larkin and Scowcroft, (1981) Theor. Appl. Genet. 60, 197-214). Similarly, the methods of preparing cell cultures are known in the art.

"Regeneration" refers to the development of a plant from cell culture or tissue culture or vegetative propagation.

"Vegetative propagation," "vegetative reproduction," or "clonal propagation" are used interchangeably herein and mean a method of taking a part of a plant and allowing that plant part to form at least roots, and also refer to the plant or plantlet obtained by that method. Optionally, the vegetative propagation is grown into a mature plant. The skilled person is aware of what plant parts are suitable for use in the method.

"Crossing" refers to the mating of two parent plants. The term encompasses "cross-pollination" and "selfing".

"Selfing" refers to self-pollination of a plant, i.e., the transfer of pollen from the anther to the stigma of the same plant.

"Cross-pollination" refers to the fertilization by the union of two gametes from different plants.

"Backcrossing" is a traditional breeding technique used to introduce a trait into a plant line or variety. The plant containing the trait is called the donor plant and the plant into which the trait is transferred is called the recurrent parent. An initial cross is made between the donor parent and the recurrent parent to produce a progeny plant. Progeny plants which have the trait are then crossed to the recurrent parent. After several generations of backcrossing and/or selfing the recurrent parent comprises the trait of the donor. The plant generated in this way may be referred to as a "single trait converted plant". The technique can also be used on a parental line of a hybrid.

"Progeny" as used herein refers to a plant obtained from a plant designated NUN 89733 CAC. A progeny may be obtained by regeneration of cell culture or tissue culture or parts of a plant of said variety or selfing of a plant of said variety or by producing seeds of a plant of said variety. In further aspects, progeny may also encompass plants obtained from crossing of at least one plant of said variety with another carrot plant of the same variety or another variety or (breeding) line, or with wild carrot plants. A progeny may comprise a mutation or a transgene. A "first generation progeny" or is the progeny directly derived from, obtained from, obtainable from or derivable from the parent plant by, e.g., traditional breeding methods (selfing and/or cross-pollinating) or regeneration (optionally combined with transformation or mutation). Thus, a plant of carrot variety NUN 89733 CAC is the male parent, the female parent or both of a first generation progeny of carrot variety NUN 89733 CAC. Progeny may have all the physiological and morphological characteristics of variety NUN 89733 CAC, when grown under the same environmental conditions. Using common breeding methods such as backcrossing or recurrent selection, mutation or transformation, one or more specific characteristics may be introduced into said variety, to provide a plant comprising all but 1, 2, or 3 or more of the morphological and physiological characteristics of carrot variety NUN 89733 CAC (e.g., as listed in Tables 1 and 2).

The terms "gene converted" or "conversion plant" or "single locus converted plant" in this context refer to carrot plants which are developed by traditional breeding techniques, e.g., backcrossing or via genetic engineering or through mutation breeding, wherein essentially all of the desired morphological and physiological characteristics of the parent variety or line are recovered, in addition to the one or more characteristics introduced into the parent transferred into the parent via e.g., the backcrossing technique (optionally including reverse breeding or reverse synthesis of breeding lines). It is understood that only the addition of a further characteristics (e.g., addition of gene conferring a further characteristic, such as a disease resistance gene), but also the replacement/modification of an existing characteristics by a different characteristic is encompassed herein (e.g., mutant allele of a gene can modify the phenotype of a characteristic).

Likewise, a "Single Locus Converted (Conversion) Plant" refers to plants developed by plant breeding techniques comprising or consisting of mutation and/or by genetic transformation and/or by traditional breeding techniques, such as backcrossing, wherein essentially all of the desired morphological and physiological characteristics of a carrot variety are recovered in addition to the characteristics of the single locus having been transferred into the variety via the backcrossing technique, or wherein the morphological and physiological characteristic of the variety has been replaced/modified in the variety. In case of a hybrid, the gene may be introduced in the male or female parental line.

"Transgene" refers to a genetic locus comprising a DNA sequence which has been introduced into the genome of a carrot plant by transformation. A plant comprising a transgene stably integrated into its genome is referred to as "transgenic plant."

As used herein, the terms "resistance" and "tolerance" are used interchangeably to describe plants that show no symptoms or significantly reduced symptoms to a specified biotic pest, pathogen, abiotic influence or environmental condition compared to a susceptible plant. These terms are optionally also used to describe plants showing some symptoms but that are still able to produce marketable product with an acceptable yield.

DETAILED DESCRIPTION OF VARIOUS ASPECTS OF THE DISCLOSURE

The disclosure relates to the plant of carrot variety NUN 89733 CAC, wherein a representative sample of seeds of said carrot variety has been deposited under the Budapest Treaty, with Accession number NCIMB 44118. NUN 89733 CAC is a purple imperator-shaped carrot variety for the fresh market and is suitable for the open field.

The disclosure further relates to carrot variety NUN 89733 CAC, which when compared to its Reference Variety has the following distinguishing characteristics as shown in Table 3: 1) semi-erect plant top habit; 2) shorter plant top; 3) medium leaf blade division; 4) shorter blade without petiole; 4) without petiole pubescence; 5) shorter leaf including petiole; 6) shorter petiole; 7) smaller core (xylem) thickness; 8) shorter root length minus taproot; 9) longer taproot; 10) smaller root shoulder; 11) smaller root at midpoint; 12) very smooth surface; 13) absent or very weak root ridging of surface; 14) absent or very small extent of green coloration in longitudinal section; 15) lighter root weight; 16) darker purple color of below ground exterior shoulder; 17) darker purple color of below ground exterior skin color; 18) lighter yellow color of cross-section xylem (core); 19) light purple color of cross-section phloem (cortex); 20) medium intensity of core color; 21) light intensity of cortex color; and 22) dark intensity of external color, when determined at 5% significance level for numerical characteristics and determined by type or degree for non-numerical characteristics, when grown under the same environmental conditions. Also encompassed are parts of that plant.

The disclosure also provides a carrot plant or part thereof having all of the physiological and morphological characteristics of carrot variety NUN 89733 CAC when grown under the same environmental conditions.

In another aspect, the plant of carrot variety NUN 89733 CAC or part thereof, comprises all of the morphological and/or physiological characteristics (i.e., average values for numerical characteristics and same type or degree for non-numerical characteristics, as indicated on the USDA Objective description of variety—carrot (unless indicated otherwise)) as shown in Tables 1 and 2, where the numerical characteristics are determined at the 5% significance level and determined by type/degree for non-numerical characteristics, when grown under the same environmental conditions. A part of this plant is provided.

The disclosure further provides a carrot plant which does not differ from the physiological and morphological characteristics of the plant of carrot variety NUN 89733 CAC as determined at the 1%, 2%, 3%, 4% or 5% significance level for numerical characteristics and identical for non-numerical characteristics when grown under the same environmental conditions. In a particular aspect, the plants are measured in the same trial (e.g., the trial is conducted as recommended by the USDA or UPOV). The disclosure also comprises a part of said plant, preferably a root or a part thereof.

The morphological and/or physiological differences between two different individual plants described herein (e.g., between carrot variety NUN 89733 CAC and a progeny of said carrot variety) or between a plant of carrot variety NUN 89733 CAC, or progeny of said variety, or a plant having all, or all but 1, 2, or 3 of the physiological and morphological characteristics of carrot variety NUN 89733 CAC and another known variety can easily be established by growing said variety next to each other or next to the other variety (in the same field, under the same environmental conditions (in the same field, optionally, next to each other), preferably in repeated several locations which are suitable for cultivation of carrots, and measuring morphological and/or physiological characteristics of a representative number of plants (e.g., to calculate an average value and to determine the variation range/uniformity within the variety). For example, trials can be carried out in Acampo Calif., USA (N 38 degrees 07'261"/W 121 degrees 18' 807", USA), whereby various characteristics, for example, market maturity, days from seeding to harvest, plant habit, leaf color, blade divisions, petiole anthocyanin, root length, root shape, root collar, root halo, root shoulder, number of secondary root scars, disease resistance, insect resistance, can be measured and directly compared for species of carrot.

Thus, the disclosure comprises carrot plant having one, two, or three physiological and/or morphological characteristics which are different from those of the plant of carrot variety NUN 89733 CAC and which otherwise has all the physiological and morphological characteristics of the plant of carrot variety NUN 89733 CAC (e.g., at 5% significance level for numerical characteristic and identical for non-numerical characteristics) for plants grown under the same environmental conditions. In another aspect, the different characteristic is the result of a mutation (e.g., spontaneous mutation or human induced mutation through e.g., targeted mutagenesis or traditional mutagenesis such as chemically or radiation induced mutagenesis) or it is the result of a transformation.

The disclosure relates to a seed of carrot variety NUN 89733 CAC wherein a representative sample of said seed has been deposited under the Budapest Treaty, with Accession number NCIMB 44118.

In another aspect, a seed of hybrid carrot variety NUN 89733 CAC is obtainable by crossing the male parent of carrot variety NUN 89733 CAC with the female parent of carrot variety NUN 89733 CAC, and harvesting the seeds produced on the female parent. The resultant seeds of said variety can be grown to produce plants of said variety.

The disclosure also provides a carrot plant grown from a seed of carrot variety NUN 89733 CAC and a plant part thereof.

The disclosure further provides a carrot root produced on a plant grown from a seed of carrot variety NUN 89733 CAC.

The disclosure also provides for a carrot plant part of variety NUN 89733 CAC, preferably a root or part thereof, a representative sample of seed from said variety has been deposited under the Budapest Treaty, with Accession number NCIMB 44118.

Also provided is a plant of carrot variety NUN 89733 CAC, or a root or other plant part thereof, produced from a seed, wherein a representative sample of said seeds has been deposited under the Budapest Treaty, with Accession Number NCIMB 44118.

Also provided is a plant part obtained from carrot variety NUN 89733 CAC, wherein said plant part is a root, or a part of a root, a harvested root, a taproot, a root tip, a fruit, a harvested fruit, a part of a fruit, a leaf, a part of a leaf, pollen, an ovule, a cell, a petiole, a shoot or a part thereof, a stem or a part thereof, a cutting, a seed, a part of a seed, seed coat or another maternal tissue which is part of a seed grown on said variety, a hypocotyl, a cotyledon, a pistil, an anther, and a flower or a part thereof. Such plant parts may be suitable for sexual reproduction (e.g., a pollen, a flower or a part thereof), vegetative reproduction (e.g., a cutting, a root, a stem, a cell, a protoplast, a leaf, a cotyledon, a meristem, etc.), or tissue culture (e.g., a leaf, a pollen, an embryo, a cotyledon, a hypocotyl, a cell, a root, a root tip, an anther, a flower, a seed, a stem, etc.). Roots are particularly important plant parts.

In a further aspect, the plant part obtained from carrot variety NUN 89733 CAC is a cell, optionally a cell in a cell or tissue culture. That cell may be grown into a plant of carrot variety NUN 89733 CAC. A part of carrot variety NUN 89733 CAC (or of progeny of that variety or of a plant having all physiological and/or morphological characteristics but one, two, or three which are different from those of carrot variety NUN 89733 CAC) further encompasses any cells, tissues, organs obtainable from the seedlings or plants in any stage of maturity.

The disclosure also provides a tissue or cell culture comprising cells of carrot variety NUN 89733 CAC. Such a tissue culture can, for example, be grown on plates or in liquid culture, or be frozen for long term storage. The cells of carrot variety NUN 89733 CAC used to start the culture can be selected from any plant part suitable for vegetative reproduction, or in a particular aspect can be selected from an embryo, a meristem, a cotyledon, a hypocotyl, pollen, a leaf, an anther, a root, a root tip, a pistil, a petiole, a flower, a fruit, a seed, a stem and a stalk. In another particular aspect, the tissue culture does not contain somaclonal variation or has reduced somaclonal variation. The skilled person is familiar with methods to reduce or prevent somaclonal variation, including regular reinitiation.

In another aspect, the disclosure provides a carrot plant regenerated from the tissue or cell culture of carrot variety NUN 89733 CAC, wherein the regenerated plant is not significantly different from carrot variety NUN 89733 CAC in all, or all but one, two, or three, of the physiological and morphological characteristics (e.g., determined at the 5% significance level for numerical characteristics and determined by degree/type for non-numerical characteristics) when grown under the same environmental conditions. Optionally, the plant has one, two, or three the physiological and morphological characteristics that are affected by a mutation or transformation with a transgene.

In another aspect, the disclosure provides a carrot plant regenerated from the tissue or cell culture of carrot variety NUN 89733 CAC, wherein the plant has all of the physiological and morphological characteristics of said variety determined (e.g., determined at the 5% significance level for numerical characteristics and determined by degree/type for non-numerical characteristics) when grown under the same environmental conditions. Similarity or difference of a characteristic is determined by measuring the characteristics of a representative number of plants grown under the same environmental conditions, determining whether type/degree characteristics are the same or different and determining whether numerical characteristics are different at the 5% significance level.

Carrot variety NUN 89733 CAC, or its progeny, or a plant having all physiological and/or morphological characteristics but one, two, or three which are different from those of carrot variety NUN 89733 CAC can also be reproduced using vegetative reproduction methods. Therefore, the disclosure provides for a method of producing a plant or a plant part of carrot variety NUN 89733 CAC, comprising vegetative propagation of carrot variety NUN 89733 CAC. Vegetative propagation comprises regenerating a whole plant from a plant part of carrot variety NUN 89733 CAC or from a progeny or from or a plant having all physiological and/or morphological characteristics of said variety but one, two, or three different characteristics, such as a cutting, a cell culture, or a tissue culture.

The disclosure also provides methods of vegetatively propagating a part of the plant of carrot variety NUN 89733 CAC. In certain aspects, the method comprises: (a) collecting tissue or cells capable of being propagated from carrot variety NUN 89733 CAC to obtain proliferated shoots; (b) rooting said proliferated shoots to obtain rooted plantlets. Steps (a) and (b) may also be reversed, i.e., first cultivating said tissue to obtain roots and then cultivating the tissue to obtain shoots, thereby obtaining rooted plantlets. The rooted plantlets may then be further grown, to obtain plants. In one aspect, the method further comprises step (c) growing plants from said rooted plantlets. Therefore, the method also comprises regenerating a whole plant from said part of carrot variety NUN 89733 CAC. In a particular aspect, the part of the plant to be propagated is a cutting, a cell culture, or a tissue culture.

The disclosure also provides for a vegetatively propagated plant of carrot variety NUN 89733 CAC (or from progeny of said variety or from or a plant having all but one, two, or three physiological and/or morphological characteristics of carrot variety NUN 89733 CAC), wherein the plant has all of the morphological and physiological characteristics of carrot variety NUN 89733 CAC (e.g., determined at the 5% significance level for numerical characteristics and determined by type/degree for non-numerical characteristics) for plants grown under the same environmental conditions. In another aspect, the propagated plant has all but one, two, or three of the morphological and physiological characteristics of carrot variety NUN 89733 CAC, e.g., determined at the 5% significance level for numerical characteristics and determined by type/degree for non-numerical characteristics for plants grown under the same environmental conditions. A part of said propagated plant or said propagated plant with one, two, or three differences is also provided. In another aspect, the propagated plant has all or all but one, two, or three of the morphological and physiological characteristics of carrot variety NUN 89733 CAC, e.g., as listed in Tables 1 and 2.

In another aspect, the disclosure provides a method for producing a carrot plant part, preferably a root or part thereof, comprising growing the plant of carrot variety NUN 89733 CAC until it develops a root, and collecting the root. Preferably, the root is collected at harvest maturity. In another aspect, the root is collected at baby stage. A plant of carrot variety NUN 89733 CAC can be produced by seeding directly in the soil (e.g., field) (see, e.g., Nunez, et. al., University of California Agriculture and Natural Resources Communication Services, Publication 7226, 1-5).

In still another aspect, the disclosure provides a method of producing a carrot plant, comprising crossing a plant of carrot variety NUN 89733 CAC with a second carrot plant at least once, allowing seed to develop and optionally harvesting said respective progeny seed. The skilled person can select progeny from said crossings. Optionally, the respective progeny is crossed twice, thrice, or four, five, six, or seven times, and allowed to set seed. In another aspect, the first step in "crossing" comprises planting seeds of a first and a second parent carrot plant, often in proximity so that pollination will occur, for example, mediated by insect vectors. Alternatively, pollen can be transferred manually. Where the plant is self-pollinated, pollination may occur without the need for direct human intervention other than plant cultivation. After pollination the plant can produce seed.

The disclosure also provides a method for collecting pollen of carrot variety NUN 89733 CAC, comprising collecting the pollen from a plant of carrot variety NUN 89733 CAC. Alternatively, the method comprises growing a plant of carrot variety NUN 89733 CAC until at least one flower contains pollen and collecting the pollen. In a particular aspect, the pollen is collected when it is mature or ripe. A suitable method for collecting pollen comprises collecting anthers or the part of the anther that contains pollen, for example, by cutting it off. Pollen can be collected in containers. Optionally, collected pollen can be used to pollinate a carrot flower.

In yet another aspect, the disclosure provides a method of producing a plant, comprising selfing a plant of carrot variety NUN 89733 CAC one or more times, and selecting a progeny plant from said selfing. In one aspect, the progeny plant retains all or all but one, two, or three of the morphological and physiological characteristics of carrot variety NUN 89733 CAC, when grown under the same environmental conditions. In a different aspect, the progeny plant, comprises all (or all but one, two or three) of the physiological and morphological characteristic of carrot variety NUN 89733 CAC, as listed in Tables 1 and 2.

The disclosure also provides a method for developing a carrot plant in a carrot breeding program, using a carrot plant of variety NUN 89733 CAC, or its parts as a source of plant breeding material. Suitable plant breeding techniques are recurrent selection, backcrossing, pedigree breeding, mass selection, mutation breeding and/or genetic marker enhanced selection. In one aspect, the method comprises crossing carrot variety NUN 89733 CAC or progeny of said variety, or a plant comprising all but 1, 2, or 3 or more of the morphological and physiological characteristics of carrot variety NUN 89733 CAC (e.g., as listed in Tables 1 and 2) with a different carrot plant, and wherein one or more offspring of the crossing are subject to one or more plant breeding techniques: recurrent selection, backcrossing, pedigree breeding, mass selection, mutation breeding and genetic marker enhanced selection (see, e.g., Stein and Nothnagel, (1995) Plant Breeding 114, 1-11). For breeding methods in general, see, e.g., Principles of Plant Genetics and Breeding, 2007, George Acquaah, Blackwell Publishing, ISBN-13: 978-1-4051-3646-4.

In another aspect, the disclosure provides a progeny plant of carrot variety NUN 89733 CAC such as a progeny plant obtained by further breeding that variety. Further breeding with carrot variety NUN 89733 CAC, includes selfing that variety and/or cross-pollinating that variety with another carrot plant or variety one or more times. In a particular aspect, the disclosure provides for a progeny plant that retains all or all but one, two, or three of the morphological and physiological characteristics of carrot variety NUN 89733 CAC, optionally all or all but one, two, or three characteristics as listed in Tables 1 and 2, determined at the 5% significance level for numerical characteristics and determined by type/degree for non-numerical characteristics, when grown under the same environmental conditions. In another aspect, the progeny is a first generation progeny, i.e., the ovule or the pollen (or both) used in the crossing is an ovule or pollen of carrot variety NUN 89733 CAC, i.e., the pollen comes from an anther of carrot variety NUN 89733 CAC, and the ovule comes from an ovary of carrot variety NUN 89733 CAC.

In another aspect, the plant and plant parts of carrot variety NUN 89733 CAC and progeny of said variety are provided, e.g., grown from seeds, produced by sexual or vegetative reproduction, regenerated from the above-described plant parts, or regenerated from a cell or tissue culture of carrot variety NUN 89733 CAC, in which the reproduced (seed propagated or vegetatively propagated) plant has all of the physiological and morphological characteristics of carrot variety NUN 89733 CAC, e.g., as listed in Tables 1 and 2. In one aspect, said progeny of carrot variety can be modified in one, two, or three characteristics, in which the modification is a result of mutagenesis or transformation with a transgene.

In one aspect, pedigree selection is used as a breeding method for developing a carrot variety. Pedigree selection is also known as the "Vilmorin System of Selection," see, e.g., Allard, John Wiley & Sons, Inc., 1999, 64-67. In general, selection is first practiced among F2 plants. In the next season, the most desirable F3 lines are first identified, then desirable F3 plants within each line are selected. The following season and in all subsequent generations of inbreeding, the most desirable families are identified first, then desirable lines within the selected families are chosen. A family refers to lines that were derived from plants selected from the same progeny from the preceding generation.

Using pedigree method, two parents may be crossed using an emasculated female and a pollen donor (male) to produce F1 offspring. In order to optimize crossing, a method of misting may be used to wash the pollen off prior to fertilization to assure crossing or hybridization. The F1 may be self-pollinated to produce segregating F2 generation. Individual plants may then be selected which represent the desired phenotype in each generation (F3, F4, F5, etc.) until the traits are homozygous or fixed within a breeding population.

Thus, progeny in connection with pedigree selection are either the generation (seeds) produced from the first cross (F1) or selfing (S1), or any further generation produced by crossing and/or selfing (F2, F3, F4, F5, F6, F7, etc.) and/or backcrossing (BC1, BC2, BC3, BC4, BC5, BC6, BC7, etc.) one or more selected plants of the F1 and/or S1 and/or BC1 generation (or plants of any further generation, e.g., the F2) with another carrot plant (an/or with wild relative of carrot).

The disclosure also provides for a method of producing a new carrot plant. The method comprises crossing a plant of carrot variety NUN 89733 CAC, or a plant comprising all but 1, 2, or 3 of the morphological and physiological characteristics of carrot variety NUN 89733 CAC (e.g., as listed in Tables 1 and 2), or a progeny plant thereof, either as male or as female parent, with a second carrot plant (or a wild relative of carrot) one or more times, and/or selfing a carrot plant of variety NUN 89733 CAC, or a progeny plant thereof, one or more times, and selecting progeny from said crossing and/or selfing. The second carrot plant may, for example, be a line or variety of the species *Daucus carota*, or other *Daucus* species or even other Apiaceae species.

In a further aspect, carrot variety NUN 89733 CAC is used in crosses with other or different carrot varieties to produce first generation (F1) carrot hybrid seeds and plants with superior characteristics. In a particular aspect, the disclosure provides a method of producing a hybrid carrot seed comprising crossing a first parent carrot plant with a second parent carrot plant and harvesting the resultant seed, in which the first parent carrot plant or second parent carrot plant is carrot variety NUN 89733 CAC. Also provided is a hybrid carrot seed produced from crossing a first parent carrot plant with a second parent carrot plant and harvesting the resultant hybrid carrot seed, wherein said first parent carrot plant or second parent carrot plant is carrot variety NUN 89733 CAC. In a further aspect, the hybrid carrot plant produce from the hybrid carrot seed is provided.

The morphological and physiological characteristics of carrot variety NUN 89733 CAC are provided, for example, in Tables 1 and 2, as collected in a trial according to USDA and/or UPOV standards. Encompassed herein is also a plant obtainable from carrot variety NUN 89733 CAC (e.g., by selfing and/or crossing and/or backcrossing with said variety and/or progeny of said variety) comprising all or all but one, two, or three of the physiological and morphological characteristics of carrot variety NUN 89733 CAC, as listed in Tables 1 and 2 (e.g., determined at the 5% significance level for numerical characteristics and determined by type/degree for non-numerical characteristics) when grown under the same environmental conditions and/or comprising one or more (or all; or all except one, two, or three) characteristics when grown under the same environmental conditions. The morphological and/or physiological characteristics may vary somewhat with variation in the environment (e.g., temperature, light intensity, day length, humidity, soil, fertilizer use, disease vectors), which is why a comparison under the same environmental conditions is preferred. Colors can best be measured using Royal Horticultural Society (RHS) Chart.

In still another aspect, the disclosure provides a method of producing a plant derived from carrot variety NUN 89733 CAC, the method comprising: (a) preparing a progeny plant derived from carrot variety NUN 89733 CAC by crossing a plant of variety NUN 89733 CAC either as a male or female parent with a second plant or selfing carrot variety NUN 89733 CAC or vegetative reproduction of carrot variety NUN 89733 CAC, and (b) collecting seeds from said crossing or regenerating a whole plant from the vegetative cell-or tissue culture. Also provided are seeds and/or plants obtained by this method. All plants produced using carrot variety NUN 89733 CAC as a parent are within the scope of the disclosure, including plant parts derived from carrot variety NUN 89733 CAC.

In a further aspect, the method comprises growing a progeny plant of a subsequent generation from said seed of a progeny plant of a subsequent generation and crossing the progeny plant of a subsequent generation with itself or a second plant and repeating the steps for an additional 3-10 generations to produce a plant derived from carrot variety NUN 89733 CAC. The plant derived from carrot variety NUN 89733 CAC may be an inbred line and the aforementioned repeating crossing steps may be defined as comprising sufficient inbreeding to produce the inbred line. By selecting plants having one or more desirable traits, a plant derived from carrot variety NUN 89733 CAC is obtained which has some of the desirable traits of the line as well as potentially other selected traits.

The disclosure provides for methods of producing plants which retain all the morphological and physiological characteristics of a plant described herein. The disclosure provides also for methods of producing a plant comprising all but 1, 2, or 3 or more of the morphological and physiological characteristics of carrot variety NUN 89733 CAC (e.g., as listed in Tables 1 and 2), but which are still genetically closely related to said carrot variety. The relatedness can, for example, be determined by fingerprinting techniques (e.g., making use of isozyme markers and/or molecular markers such as Single-nucleotide polymorphism (SNP) markers, amplified fragment length polymorphism (AFLP) markers, microsatellites, minisatellites, Random Amplified Polymorphic DNA (RAPD) markers, restriction fragment length polymorphism (RFLP) markers and others). A plant is "closely related" to carrot variety NUN 89733 CAC if its DNA fingerprint is at least 80%, 90%, 95% or 98% identical to the fingerprint of carrot variety NUN 89733 CAC. In a particular aspect, AFLP markers are used for DNA fingerprinting (see, e.g., Vos et al. 1995, Nucleic Acid Research 23: 4407-4414). A closely related plant may have a Jaccard's Similarity index of at least about 0.8, preferably at least about 0.9, 0.95, 0.98 or more (see, e.g., Shim and Jorgensen, Theor Appl Genet (2000) 101:227-233). The disclosure also provides a plant and a variety obtained or selected by applying these methods on carrot variety NUN 89733 CAC. Such a plant may be produced by traditional breeding techniques or mutation or transformation or in another aspect, a plant may simply be identified and selected amongst plants of said variety, or progeny of said variety, e.g., by identifying a variant within carrot variety NUN 89733 CAC, which variant differs from the variety described herein in one, two, or three of the morphological and/or physiological characteristics (e.g., characteristics listed in Tables 1 and 2). In one aspect, the disclosure provides a carrot plant having a Jaccard's Similarity index with carrot variety NUN 89733 CAC of at least 0.8, e.g., at least 0.85, 0.9, 0.95, 0.98 or even at least 0.99.

In another aspect, the disclosure provides a carrot plant comprising genomic DNA having at least 95%, 96%, 97%, 98% or 99% sequence identity compared to the genomic DNA sequence of a plant of carrot variety NUN 89733 CAC, as deposited under Accession Number NCIMB 44118. In one aspect, the carrot plant further comprises all or all but 1, 2, or 3 of the morphological and physiological characteristics of carrot variety NUN 89733 CAC (e.g., as listed in Tables 1 and 2). In other aspects, the carrot plant is a hybrid derived from a seed or plant of carrot variety NUN 89733 CAC.

For the purpose of this disclosure, the "sequence identity" of nucleotide sequences, expressed as a percentage, refers to the number of positions in the two optimally aligned sequences which have identical residues (×100) divided by the number of positions compared. A gap, i.e., a position in the pairwise alignment where a residue is present in one sequence but not in the other, is regarded as a position with non-identical residues. A pairwise global sequence alignment of two nucleotide sequences is found by aligning the two sequences over the entire length according to the Needleman and Wunsch global alignment algorithm described in Needleman and Wunsch, 1970, J. Mol. Biol. 48(3):443-53). A full implementation of the Needleman-Wunsch global alignment algorithm is found in the needle program in The European Molecular Biology Open Software Suite (see, e.g., EMBOSS, Rice et al., Trends in Genetics June 2000, vol. 16, No. 6. pp. 276-277).

In another aspect, the plant of carrot variety NUN 89733 CAC may also be mutated (by e.g., irradiation, chemical mutagenesis, heat treatment, etc.) and mutated seeds or plants may be selected in order to change one or more characteristics of said variety. Methods such as TILLING (Targeting Induced Local Lesions in Genomes) may be applied to carrot populations in order to identify mutants.

Similarly, carrot variety NUN 89733 CAC may be transformed and regenerated, whereby one or more chimeric genes are introduced into the variety or into a plant comprising all but 1, 2, 3, or more of the morphological and physiological characteristics (e.g., as listed in Tables 1 and 2). Many useful traits can be introduced into carrot variety NUN 89733 CAC by e.g., crossing carrot variety NUN 89733 CAC with a transgenic carrot plant comprising a desired transgene as well as by directly introducing a transgene into carrot variety NUN 89733 CAC by genetic transformation techniques.

Any pest or disease resistance genes may be introduced into carrot variety NUN 89733 CAC, progeny of said variety or into a plant comprising all but 1, 2, or 3 or more of the morphological and physiological characteristics of carrot variety NUN 89733 CAC (e.g., as listed in Tables 1 and 2). Resistance to one or more of the following diseases or pests may be introduced into plants described herein: *Alternaria* Leaf Blight (*Alternaria* dauci), Aster Yellows (Macrosteles fascifrons), Cavity Spot (*Pythium sulcatum* and *P. violae*), *Cercospora* Blight or Carrot Early Blight (Cerocospora carotae), Bacterial Blight (*Xanthomonas* carotae), Powdery Mildew (*Erysiphe heraclei*), Phytium Root Dieback (*Pythium* spp.), *Sclerotinia* Decay or Watery Soft Rot (*Sclerotinia* spp.), Cottony Soft Rot (*Sclerotinia sclerotiorum*), Southern Blight (*Sclerotium rolfsii*), Bacterial Soft Rot (Ewinia carotovora), Black Root Rot (*Alternaria* radicina), Gray Mold (*Botrytis* spp.), Sour Rot (Geothrichurn spp.), Root Knot Nematode (*Meloidogyne* spp.), Stubby Root Nematode (*Trichodorus* spp., and Paratrichodorus spp.), Needle Nematode (*Longidorus africanus*), Nutsedges Yellow (*Cyperus esculentus*), Nutsedges Purple (*C. rotundus*), Saltmarsh Catterpillars (Estigmene acrea), Cotton-melon Aphid (*Aphis gossypii*), and/or Silverleaf Whitefly (*Bemisia argentifolii*). Other resistances, against pathogenic viruses (e.g., Motley Dwarf Virus, Carrot Thin Leaf Virus), fungi, bacteria, nematodes, insects or other pests may also be introduced.

Genetic transformation may, therefore, be used to insert a selected transgene into the carrot plants of the disclosure described herein or may, alternatively, be used for the preparation of transgenic carrot plants which can be used as a source of transgene(s), which can be introduced into carrot variety NUN 89733 CAC by e.g., backcrossing. A genetic trait which has been engineered into the genome of a particular carrot plant may then be moved into the genome of another carrot plant (e.g., another variety) using traditional breeding techniques which are well known in the art. For example, backcrossing is commonly used to move a transgene from a transformed carrot variety into an already developed carrot variety and the resulting backcross conversion plant will then comprise the transgene(s).

Any DNA sequences, whether from a different species or from the same species, which are inserted into the genome using transformation, are referred herein collectively as "transgenes". A "transgene" also encompasses antisense, or sense and antisense sequences capable of gene silencing. Thus, the disclosure also related to transgenic plants of carrot variety NUN 89733 CAC. In some aspects, a transgenic plant of carrot variety NUN 89733 CAC may contain at least one transgene but could also contain at least 1, 2, 3, 4, or more transgenes.

Plant transformation involves the construction of an expression vector which will function in plant cells. Such a vector comprises DNA comprising a gene under control of, or operatively linked to a regulatory element active in plant cells (e.g., promoter). The expression vector may contain one or more such operably linked gene/regulatory element combinations. The vector may be in the form of a plasmid and can be used alone or in combination with other plasmids to provide transformed carrot plants using transformation methods to incorporate transgenes into the genetic material of the carrot plant(s). Transformation can be carried out using standard methods, such as *Agrobacterium tumefaciens* mediated transformation or biolistics, followed by selection of the transformed cells and regeneration into plants.

Plants can also be genetically engineered, modified, or manipulated to express various phenotypes of horticultural interest. Through the transformation of carrot, the expression of genes can be altered to enhance disease resistance, insect resistance, herbicide resistance, stress tolerance, horticultural quality, and other traits. Transformation can also be used to insert DNA sequences which control or help control male sterility or fertility restoration. DNA sequences native to carrot as well as non-native DNA sequences can be transformed into carrot and used to alter levels of native or non-native traits. Various promoters, targeting sequences, enhancing sequences, and other DNA sequences can be inserted into the genome for the purpose of altering the expression of proteins. Reduction of activity of specific genes (also known as gene silencing or gene suppression) is desirable for several aspects of genetic engineering in plants.

Genome editing is another method recently developed to genetically engineer plants. Specific modification of chromosomal loci or targeted mutation can be done through sequence-specific nucleases (SSNs) by introducing a targeted DNA double strand break in the locus to be altered. Examples of SSNs that have been applied to plants are: finger nucleases (ZFNs), transcription activator-like effector nucleases (TALENs), engineered homing endonucleases or meganucleases, and clustered regularly interspaced short palindromic repeats (CRISPR)/CRISPR-associated protein 9 (Cas9), see, e.g., Songstad, et. al., Critical Reviews in Plant Sciences, 2017, 36:1, 1-23.

Thus, the disclosure provides a method of producing a carrot plant having a desired trait, comprising mutating the plant or plant part of carrot variety NUN 89733 CAC, optionally with a target gene, and selecting a plant with the desired trait, wherein the mutated plant otherwise comprises the desired trait and has all or all but one, two, or three of the physiological and morphological characteristics of said carrot variety, optionally as described in Tables 1 and 2, wherein a representative sample of seed of carrot variety NUN 89733 CAC has been deposited under Accession Number NCIMB 44118. In a further aspect, the desired trait is yield, size, shape, color, flavor or taste, storage properties, nutritional quality, post-harvest quality, male sterility, herbicide tolerance, insect resistance, pest resistance, disease resistance, environmental stress tolerance, modified carbohydrate metabolism, modified protein metabolism, or ripening.

The disclosure also provides a method for inducing a mutation in carrot variety NUN 89733 CAC comprising:
  a. exposing the seed, plant, plant part, or cell of carrot variety NUN 89733 CAC to a mutagenic compound or to radiation, wherein a representative sample of seed of carrot variety NUN 89733 CAC is deposited under Accession Number NCIMB 44118;
  b. selecting the seed, plant, plant part, or cell of carrot variety NUN 89733 CAC having a mutation; and c. optionally growing and/or multiplying the seed, plant, plant part, or cell of carrot variety NUN 89733 CAC, having the mutation.

The disclosure also provides a method of producing a carrot plant having a desired trait, wherein the method comprises transforming the carrot plant with a transgene that confers the desired trait, wherein the transformed plant otherwise comprises the desired trait and has all of the physiological and morphological characteristic of the plant of variety NUN 89733 CAC. Thus, a transgenic carrot plant is provided which is produced by the method described above, wherein the plant comprises the desired trait and has all of the physiological and morphological characteristics of carrot variety NUN 89733 CAC.

In another aspect, the disclosure provides a method of producing a progeny of plant of variety NUN 89733 CAC further comprising a desired trait, said method comprising transforming the plant of carrot variety NUN 89733 CAC with at least one transgene that confers the desired trait and/or crossing the plant of carrot variety NUN 89733 CAC with a transgenic carrot plant comprising a desired transgene so that the genetic material of the progeny that resulted from the cross contains the desired transgene(s). Also encompassed is the progeny produced by this method.

A desired trait (e.g., gene(s)) conferring pest or disease resistance, herbicide, fungicide or insecticide tolerance, etc.) can be introduced into carrot variety NUN 89733 CAC, or progeny of said variety, by transforming said variety or progeny of said variety with a transgene that confers the desired trait, wherein the transformed plant otherwise comprises the desired trait and has all or all but one, two, or three of the physiological and/or morphological and/or physiological characteristics of carrot variety NUN 89733 CAC, or the progeny of said variety. In another aspect, the transformation or mutation confers yield, size, shape, color, flavor or taste, storage properties, nutritional quality, post-harvest quality, male sterility, herbicide tolerance, insect resistance, pest resistance, disease resistance, environmental stress tolerance, modified carbohydrate metabolism, modified protein metabolism, or ripening. In a particular aspect, the specific transgene may be any known in the art or listed herein, including, a polynucleotide sequence conferring resistance to imidazolinone, sulfonylurea, glyphosate, glufosinate, triazine, benzonitrile, cyclohexanedione, phenoxy proprionic acid and L-phosphinothricin or a polynucleotide conferring resistance to *Alternaria* Leaf Blight (*Alternaria dauci*), Aster Yellows (Macrosteles fascifrons), Cavity Spot (*Pythium sulcatum* and *P. violae*), *Cercospora* Blight or Carrot Early Blight (Cerocospora carotae), Bacterial Blight (*Xanthomonas* carotae), Powdery Mildew (*Erysiphe heraclei*), Phytium Root Dieback (*Pythium* spp.), *Sclerotinia* Decay or Watery Soft Rot (*Sclerotinia* spp.), Cottony Soft Rot (*Sclerotinia sclerotiorum*), Southern Blight (*Sclerotium rolfsii*), Bacterial Soft Rot (Ewinia *carotovora*), Black Root Rot (*Alternaria* radicina), Gray Mold (*Botrytis* spp.), Sour Rot (Geothrichurn spp.), Root Knot Nematode (*Meloidogyne* spp.), Stubby Root Nematode (*Trichodorus* spp., and Paratrichodorus spp.), Needle Nematode (*Longidorus africanus*), Nutsedges Yellow (*Cyperus esculentus*), Nutsedges Purple (*C. rotundus*), Saltmarsh Catterpillars (Estigmene acrea), Cotton-melon Aphid (*Aphis gossypii*), and/or Silverleaf Whitefly (*Bemisia* argentifolii). Other resistances, against pathogenic viruses (e.g., Motley Dwarf Virus, Carrot Thin Leaf Virus), fungi, bacteria, nematodes, insects or other pests may also be introduced.

By crossing and/or selfing, (one or more) single traits may be introduced into the carrot variety NUN 89733 CAC (e.g., using backcrossing breeding schemes), while retaining the remaining morphological and physiological characteristics of said variety and/or while retaining one or more or all distinguishing characteristics. A single trait converted plant may thereby be produced. For example, disease resistance genes may be introduced, genes responsible for one or more quality traits, yield, etc. Both single genes (e.g., dominant or recessive) and one or more QTLs (quantitative trait loci) may be transferred into NUN 89733 CAC by breeding with said variety.

In another aspect, the disclosure provides a method of introducing a single locus conversion, single trait conversion, or a desired trait into carrot variety NUN 89733 CAC, comprising introducing a single locus conversion, single trait conversion, or a desired trait in at least one of the parents of carrot variety NUN 89733 CAC, and crossing the converted parent with the other parent of carrot variety NUN 89733 CAC to obtain seed of said carrot variety.

In another method, the step of introducing a single locus conversion, single trait conversion, or a desired trait in at least one of the parent plants comprises:

a. crossing the parental line of carrot variety NUN 89733 CAC with a second carrot plant comprising the single locus conversion, the single trait conversion or the desired trait;

b. selecting F1 progeny plants that contain the single locus conversion, the single trait conversion or the desired trait;

c. crossing said selected progeny plants of step b) with the parental line of step a), to produce a backcross progeny plant;

d. selecting backcross progeny plants comprising the single locus conversion, the single trait conversion or the desired trait and otherwise all or all but one, two or three of the morphological and physiological characteristics the parental line of step a) to produce selected backcross progeny plants; and e. optionally repeating steps c) and d) one or more times in succession to produce selected second, third or fourth or higher backcross progeny plants comprising the single locus conversion, the single trait conversion or the desired trait and otherwise all or all but one, two, or three of the morphological and physiological characteristics the parental line of step a) to produce selected backcross progeny plants, when grown in the same environmental conditions.

The disclosure further relates to plants obtained by this method.

In another aspect, introducing a single locus conversion, a single trait conversion, or a desired trait in at least one of the parents comprise:

a. obtaining a cell or tissue culture of cells of the parental line of carrot variety NUN 89733 CAC;

b. genetically transforming or mutating said cells;

c. growing the cells into a plant; and d. optionally selecting plants that contain the single locus conversion, the single trait conversion, or the desired trait.

In another aspect, the disclosure provides a method of introducing a single locus conversion, a single trait conversion, or a desired trait into carrot variety NUN 89733 CAC comprising:

a. obtaining a combination of a parental lines of carrot variety NUN 89733 CAC, optionally through reverse synthesis of breeding lines;

b. introducing a single locus conversion, a single trait conversion, or a desired trait in at least one of the parents of step a; and
c. crossing the converted parent with the other parent of step a to obtain seed of carrot variety NUN 89733 CAC.

In any of the above methods, wherein the single locus conversion concerns a trait, the trait may be yield or pest resistance or disease resistance. In one aspect, the trait is disease resistance and the resistance is conferred to *Alternaria* Leaf Blight (*Alternaria* dauci), Aster Yellows (Macrosteles fascifrons), Cavity Spot (*Pythium sulcatum* and *P. violae*), *Cercospora* Blight or Carrot Early Blight (Cerocospora carotae), Bacterial Blight (*Xanthomonas* carotae), Powdery Mildew (*Erysiphe heraclei*), Phytium Root Dieback (*Pythium* spp.), *Sclerotinia* Decay or Watery Soft Rot (*Sclerotinia* spp.), Cottony Soft Rot (*Sclerotinia sclerotiorum*), Southern Blight (*Sclerotium rolfsii*), Bacterial Soft Rot (Ewinia *carotovora*), Black Root Rot (*Alternaria radicina*), Gray Mold (*Botrytis* spp.), Sour Rot (Geothrichurn spp.), Root Knot Nematode (*Meloidogyne* spp.), Stubby Root Nematode (*Trichodorus* spp., and Paratrichodorus spp.), Needle Nematode (*Longidorus africanus*), Nutsedges Yellow (*Cyperus esculentus*), Nutsedges Purple (*C. rotundus*), Saltmarsh Catterpillars (Estigmene acrea), Cotton-melon Aphid (*Aphis gossypii*), and/or Silverleaf Whitefly (*Bemisia argentifolii*). Other resistances, against pathogenic viruses (e.g., Motley Dwarf Virus, Carrot Thin Leaf Virus), fungi, bacteria, nematodes, insects or other pests may also be introduced.

The disclosure also provides a plant having one, two, or three physiological and/or morphological characteristics which are different from those of carrot variety NUN 89733 CAC, and which otherwise has all the physiological and morphological characteristics of said carrot variety, wherein a representative sample of seed of carrot variety NUN 89733 CAC has been deposited under Accession Number NCIMB 44118. In particular, variants which differ from carrot variety NUN 89733 CAC in none, one, two or three of the characteristics mentioned in Tables 1 and 2 are encompassed.

The disclosure also provides a plant having one, two, or three physiological and/or morphological characteristics which are different from those of carrot variety NUN 89733 CAC, and which otherwise has all the physiological and morphological characteristics of said carrot variety, wherein a reppresentative sample of seed of carrot variety NUN 89733 CAC has been deposited under Accession Number NCIMB 44118. In particular, variants which differ from carrot variety NUN 89733 CAC in none, one, two or three of the characteristics mentioned in Tables 1 and 2 are encompassed.

In one aspect, the disclosure provides a haploid plant and/or a doubled haploid plant of carrot variety NUN 89733 CAC, or of a plant having all but one, two, or three physiological and/or morphological characteristics of carrot variety NUN 89733 CAC, or progeny of said carrot variety. Haploid and doubled haploid (DH) plants can, for example, be produced by cell or tissue culture and chromosome doubling agents and regeneration into a whole plant. DH production chromosome doubling may be induced using known methods, such as colchicine treatment or the like. In one aspect, the method comprises inducing a cell or tissue culture with chromosome doubling agent and regenerating the cells or tissues into a whole plant.

In another aspect, the disclosure comprises method for making doubled haploid cells of carrot variety NUN 89733 CAC, comprising making doubled haploid cells from haploid cells from the plant or plant part of carrot variety NUN 89733 CAC with a chromosome doubling agent, such as colchicine treatment (see, e.g., Nikolova and Niemirowicz-Szczytt (1996) Acta Soc Bot Pol 65:311-317).

In another aspect, the disclosure provides haploid plants and/or doubled haploid plants derived from carrot variety NUN 89733 CAC that, when combined, make a set of parents of carrot variety NUN 89733 CAC. The haploid plant and/or the doubled haploid plant of carrot variety NUN 89733 CAC can be used in a method for generating parental lines of carrot variety NUN 89733 CAC.

The disclosure also relates to a method of producing a combination of parental lines of a plant of carrot variety NUN 89733 CAC, comprising the step of making doubled haploid cells from haploid cells from said plant or a seed of that plant; and optionally crossing these parental lines to produce and collect seeds. In another aspect, the disclosure relates to a combination of parental lines produced by this method. In still another aspect, the combination of parental lines can be used to produce a seed or plant of carrot variety NUN 89733 CAC when these parental lines are crossed. In still another aspect, the disclosure relates to a combination of parental lines from which a seed or plant having all physiological and/or morphological characteristics of carrot variety NUN 89733 CAC (e.g., determined at the 5% significance level for numerical characteristics and determined by type/degree for non-numerical characteristics) when grown under the same conditions.

The disclosure also provides methods for determining the identity of parental lines described herein, in particular the identity of the female line. US 2015/0126380, which is incorporated by reference, relates to a non-destructive method for analyzing maternal DNA of a seed. In this method, the DNA is dislodged from the seed coat surface and can be used to collect information on the genome of the maternal parent of the seed. This method for analyzing maternal DNA of a seed comprises the steps of contacting a seed with a fluid to dislodge DNA from the seed coat surface, and analyzing the DNA thus dislodged from the seed coat surface using methods known in the art. The skilled person is thus able to determine whether a seed has grown on a plant of a plant carrot variety NUN 89733 CAC, or is a progeny of said variety, because the seed coat of the seed is a maternal tissue genetically identical to carrot variety NUN 89733 CAC. In one aspect, the disclosure relates to a carrot seed coat comprising maternal tissue of carrot variety NUN 89733 CAC. In another particular aspect, the disclosure provides a method of identifying the female parental line of carrot variety NUN 89733 CAC by analyzing the seed coat or another maternal tissue of said seed.

In another aspect, a combination of a male and a female parental line of carrot variety NUN 89733 CAC can be generated, for example, through reverse synthesis of breeding lines.

Using methods known in the art like "reverse synthesis of breeding lines" or "reverse breeding," it is possible to produce parental lines for a hybrid plant such as carrot variety NUN 89733 CAC. A skilled person can take any individual heterozygous plant (called a "phenotypically superior plant" in Example 2 of US 2015/0245570; which is hereby incorporated by reference in its entirety; carrot variety NUN 89733 CAC is such a plant) and generate a combination of parental lines (reverse breeding parental lines) that, when crossed, produce the variety NUN 89733 CAC. It is not necessary that the reverse breeding parental lines are identical to the original parental lines. Such new breeding methods are based on the segregation of individual alleles in the spores produced by a desired plant and/or in the progeny derived from the self-pollination of that desired plant, and on the subsequent identification of suitable progeny plants in one generation, or in a limited number of inbred cycles. Such a method is known from US 2015/0245570 or from Wijnker et al., Nature Protocols Volume: 9, Pages: 761-772 (2014) DOI: doi:10.1038/nprot.2014.049. Thus, the disclosure provides a method for producing parental lines for a hybrid organism (e.g., carrot variety NUN 89733 CAC), comprises in one aspect: a) defining a set of genetic markers that are present in a heterozygous form (H) in a partially heterozygous starting organism; b) producing doubled haploid lines from spores of the starting organism: c) genetically characterizing the doubled haploid lines thus obtained for the said set of genetic markers to determine whether they are present in a first homozygous form (A) or in a second homozygous form (B); and d) selecting at least one pair of doubled haploid lines that have complementary alleles for at least a subset of the genetic markers, wherein each member of the pair is suitable as a parental line for a hybrid organism.

In another aspect, the method for producing parental lines for hybrid organisms, e.g., of carrot variety NUN 89733 CAC, which when crossed reconstitute the genome of carrot variety NUN 89733 CAC, comprising:
  a. defining a set genetic markers that are present a heterozygous form (H) in a partially heterozygous starting organism;
  b. producing at least one further generation from the starting organism by self-pollination (e.g., F2 or F3 generation);
  c. selecting at least one pair of progeny organisms in which at least one genetic marker from the set is present in a complementary homozygous form (B vs. A, or A vs. B); and
  d. optionally repeating steps b) and c) until at least one pair of progeny organisms that have complementary alleles for at least a subset of the genetic markers had been selected as parental lines for a hybrid.

In another aspect, the disclosure provides a method of determining the genotype of a plant of the disclosure comprising the step of detecting in the genome (e.g., a sample of nucleic acids) of the plant at least a first polymorphism or an allele. The skilled person is familiar with many suitable methods of genotyping, detecting a polymorphism or detecting an allele including restriction fragment length polymorphism identification (RFLP) of genomic DNA, random amplified polymorphic detection (RAPD) of genomic DNA, amplified fragment length polymorphism detection (AFLP), polymerase chain reaction (PCR), DNA sequencing, allele specific oligonucleotide (ASO) probes, and hybridization to DNA microarrays or beads. Alternatively, the entire genome could be sequenced. The method may, in certain embodiments, comprise detecting a plurality of polymorphisms in the genome of the plant, for example by obtaining a sample of nucleic acid from a plant and detecting in said nucleic acids a plurality of polymorphisms. The method may further comprise storing the results of the step of detecting the plurality of polymorphisms on a computer readable medium.

Also provided is a plant part obtainable from carrot variety NUN 89733 CAC or from progeny of said variety or from a plant having all but one, two, or three physiological and/or morphological characteristics which are different from those of carrot variety NUN 89733 CAC, or from a vegetatively propagated plant of carrot variety NUN 89733 CAC (or from its progeny or from a plant having all or all but one, two, or three physiological and/or morphological characteristics which are different from those of carrot variety NUN 89733 CAC), wherein said plant part is a root, or a part of a root, a harvested root, a taproot, a root tip, a fruit, a harvested fruit, a part of a fruit, a leaf, a part of a leaf, pollen, an ovule, a cell, a petiole, a shoot or a part thereof, a stem or a part thereof, a cutting, a seed, a part of a seed, seed-coat or another maternal tissue which is part of a seed grown on NUN 89733 CAC, or a hypocotyl, a cotyledon, a pistil, an anther, or a flower or a part thereof.

Such a plant part of carrot variety NUN 89733 CAC can be stored and/or processed further. The disclosure thus provides for a food or a feed product comprising one or more of such parts from carrot variety NUN 89733 CAC or from progeny of said variety, or from a derived variety, such as a plant having all but one, two, or three physiological and/or morphological characteristics of carrot variety NUN 89733 CAC. Preferably, the plant part is a carrot root or part thereof and/or an extract from a root or another plant part described herein comprising at least one cell of carrot variety NUN 89733 CAC. The food or feed product may be fresh or processed, e.g., dried, grinded, powdered, pickled, chopped, cooked, roasted, in a sauce, in a sandwich, pasted, puréed or concentrated, juiced, pickled, canned, steamed, boiled, fried, blanched and/or frozen including baby-carrots.

In another aspect, the disclosure provides for a carrot root of variety NUN 89733 CAC, or a part of a root of said variety. The root can be in any stage of maturity, for example, immature or mature. Marketable carrot roots are generally sorted by size, shape, color, and quality after harvest. Alternatively, carrot roots can be sorted by market segment, e.g., fresh or processing, snack (mini carrot or normal sized), bulk consumer, or food service. Also, at-harvest and/or post-harvest characteristics of roots can be compared, such as by cold storage holding quality (silvering or white scale, or browning), breakage or splitting, firmness, flavor, or bitterness can be measured using known methods.

In another aspect, the disclosure provides for a container comprising or consisting of a plurality of harvested carrot roots or parts of roots of carrot variety NUN 89733 CAC, or roots of progeny thereof, or roots of a derived variety.

In another aspect, the plant, plant part, or seed of carrot variety NUN 89733 CAC is inside one or more containers, for example, containers such as cans, boxes, crates, bags, cartons, Modified Atmosphere Packaging, films (e.g., biodegradable films), etc. comprising a plant or a part of a plant (fresh and/or processed) or a seed of carrot variety NUN 89733 CAC. In a particular aspect, the container comprises a plurality of seeds of carrot variety NUN 89733 CAC or a plurality of plant parts of carrot variety NUN 89733 CAC. The seed may be disinfected, primed and/or treated with various compounds, such as seed coatings or crop protection compounds. The seed produces a plant of carrot variety NUN 89733 CAC.

All documents (e.g., patent publications) are herein incorporated by reference in their entirety, including the following cited references:

Naktuinbow, Calibration book *Daucus carota* L, 2010.

UPOV, "Guidelines for the Conduct of Tests for Distinctness, Uniformity and Stability, TG/49/8 (Geneva 2007, last updated in 2015 Mar. 25), world-wide web at upov.int under edocs/tgdocs/en/tg049.pdf.

US Department of Agriculture, Agricultural Marketing Service, "Objective description of Variety—Carrot (*Daucus carota*)," world wide web at ams.usda.gov/services/plant-variety-protection/pvpo-c-forms, under carrot.

Acquaah, G., "Principles of Plant Genetics and Breeding", Blackwell Publishing, 2007, ISBN-13: 978-1-4051-3646-4.

Arnhold-Schmitt, B., et. al., "Physiological Aspects of Genome Variability in Tissue Culture. I. Growth Phase-Dependent Differential DNA Methylation of the Carrot Genome (*Daucus carota* L.) During Primary Culture", Theoretical and Applied Genetics, 1995, vol. 91, no. 5, pp. 809-815

Jhang, T., et. al., "Efficiency of Different Marker Systems for Molecular Characterization of Subtropical Carrot Germplasm," The Journal of Agricultural Science, 2010, vol. 148, no. 2, pp. 171-181.

Larkin, P. J., et. al., "Somaclonal Variation—A Novel Source of Variability from Cell Cultures for Plant Improvement", Theoretical and Applied Genetics, 1981, vol. 60, no. 4, pp. 197-214.

Martin, E., et al., "Identification of Markers Linked to Agronomic Traits in Globe Artichoke", Australian Journal of Crop Science, 2008, vol. 1(2), pp. 43-46.

Needleman, S. B., et. al., "A General Method Applicable to the Search for Similarities in the Amino Acid Sequence of Two Proteins", Journal of Molecular Biology, 1970, vol. 48(3), pp. 443-53.

Nikolova, V., et. al., "Diploidization of Cucumber (*Cucumis sativus* L.) Haploids by Colchini Treatment", Acta Societas Botanicorum Poloniae, 1996, vol. 65, pp. 311-317.

Nunez, et. al., "Carrot Production in California," University of California Agriculture and Natural Resources Communication Services, Publication 7226, 1997, pp. 1-5.

Rice, P., et al., "EMBOSS: The European Molecular Biology Open Software Suite", Trends in Genetics, 2000, vol. 16, Issue 6. pp. 276-277.

Shim, S. J., and Jorgensen, R. B., "Genetic Structure in Cultivated and Wild Carrots (*Daucus carota* L.) Revealed by AFLP Analysis", Theor Appl Genet, 2000, vol. 101, pp. 227-233.

Stein, M., et. al., "Some Remarks on Carrot Breeding (*Daucus carota* saativus Hoffm.), Plant Breeding, 1995, vol. 114, no. 1, pp. 1-11.

Vos, P., et al., "AFLP: A New Technique for DNA Fingerprinting", Nucleic Acids Research, 1995, vol. 23(21), pp. 4407-4414.

Wijnker, E., et al., "Hybrid Recreation by Reverse breeding in *Arabidopsis thaliana*", Nature Protocols, 2014, vol. 9, pp. 761-772. DOI: doi: 10.1038/nprot.2014.049

US 2015/0126380

US 2015/0245570

Development of Carrot Variety NUN 89733 CAC

The hybrid carrot variety NUN 89733 CAC was developed from a male and female proprietary inbred line of Nunhems. The female and male parents were crossed to produce hybrid (F1) seeds of carrot variety NUN 89733 CAC. The seeds of carrot variety NUN 89733 CAC can be grown to produce hybrid plants and parts thereof (e.g., carrot roots). The hybrid carrot variety NUN 89733 CAC can be propagated by seeds or vegetatively.

The hybrid variety is uniform and genetically stable. This has been established through evaluation of horticultural characteristics. Several hybrid seed production events resulted in no observable deviation in genetic stability. Coupled with the confirmation of genetic stability of the female and male parents the Applicant has concluded that carrot variety NUN 89733 CAC is uniform and stable.

Deposit Information

A total of 2500 seeds of the hybrid carrot variety NUN 89733 CAC was made and accepted according to the Budapest Treaty by Nunhems B.V. on Feb. 7, 2023, at the NCIMB Ltd., Ferguson Building, Craibstone Estate, Bucksburn, Aberdeen AB21 9YA, United Kingdom (NCIMB). The deposit has been assigned NCIMB number 44118. A statement indicating the viability of the sample has been provided. A deposit of carrot variety NUN 89733 CAC and of the male and female parent line is also maintained at Nunhems B.V. The seed lot number for carrot variety NUN 89733 CAC is 29809101007.

The deposit will be maintained in NCIMB for a period of 30 years, or 5 years after the most recent request, or for the enforceable life of the patent whichever is longer and will be replaced if it ever becomes nonviable during that period. Access to the deposits will be available during the pendency of this application to persons determined by the Director of the U.S. Patent Office to be entitled thereto upon request. Subject to 37 C.F.R. § 1.808(b), all restrictions imposed by the depositor on the availability to the public of the deposited material will be irrevocably removed upon the granting of the patent. Applicant does not waive any rights granted under this patent on this application or under the Plant Variety Protection Act (7 U.S.C. § 2321 et seq.). Accordingly, the requirements of 37 CFR § 1.801-1.809 have been satisfied.

Characteristics of Carrot Variety NUN 89733 CAC

The most similar variety to NUN 89733 CAC refers herein to variety NUN 89731 CAC, a commercial variety from Nunhems B.V. with commercial name, PurpleSnax.

In Tables 1 and 2, a comparison between carrot variety NUN 89733 CAC and the Reference Variety is shown based on a trial in the USA. Trial location: El Centro, Calif., USA; Harvest date: Feb. 18, 2020.

A trial of 30 plants of each variety, from which at least 15 plants or plant parts were randomly selected and were used to measure characteristics. For numerical characteristics, averages were calculated. For non-numerical characteristics, the type/degree were determined. Similarity and differences between two different plant lines or varieties can be determined by comparing the number of morphological and/or physiological characteristics that are the same (i.e., statistically not significantly different) or that are different (i.e., statistically significantly different) between the two plant lines or varieties grown under the same environmental conditions. A numerical characteristic is considered to be "the same" when the value for a numeric characteristic is not significantly different at the 1% ($p<0.01$) or 5% ($p<0.05$) significance level, using the T-Test Paired Two Sample Means, a standard method known to the skilled person. A non-numerical characteristic is considered to be "the same" when the values have the same "degree" or "type" when scored using USDA and/or UPOV descriptors, for plants are grown under the same environmental conditions. In one aspect, a statistical analysis using the T-test at 5% significance level is provided (see, Tables 4-15).

In one aspect, the disclosure provides a plant having the physiological and morphological characteristics of carrot variety NUN 89733 CAC as presented in Tables 1 and 2, when grown under the same environmental conditions.

TABLE 1

Characteristics of Carrot Variety NUN 89733 CAC and the Reference Variety (USDA Descriptors)

| Characteristics | Application Variety (NUN 89733 CAC) | Reference Variety (NUN 89731 CAC) |
|---|---|---|
| Type: Amsterdam, Flakee, Berlicum, Chantenay, Danvers, Imperator, Nantes, Other (Specify) | Color | Color |
| Plant Top (at harvest stage): | | |
| Habit: erect, semi-erect, prostrate | Semi-erect | Semi-erect to prostrate |
| Plant Top Height (from Shoulder to Top of Crown), cm | 19.80 cm | 25.57 cm |
| Plant Top Neck Diameter, mm | 11.90 mm | 12.22 mm |
| Top Attachment: Single, multiple | Single | Single |
| Leaf (at harvest stage): | | |
| Blade Color: light green, medium green, dark green; other | Medium green | Medium green |
| Color Chart Value (RHS Color Cart) | RHS 137B | RHS 137A |
| Blade division: fine, medium, coarse | Medium | Medium to coarse |
| Blade Length (Without Petiole), cm | 19.69 cm | 28.28 cm |
| Petiole Length from Crown to First Pinna, cm | 30.47 cm | 32.64 cm |
| Petiole Anthocyanin: absent, present | Absent | Absent |
| Petiole Pubescence: absent, present | Absent | Present |
| Root (at market maturity): | | |
| Cortex (Phloem) Thickness (Midpoint X-Section), mm | 5.18 mm | 5.58 mm |
| Core (Xylem) Thickness (Midpoint X-Section), mm | 8.33 mm | 10.36 mm |
| Carrot Length (Minus Taproot), cm | 22.92 cm | 24.95 cm |
| Length of Taproot, mm | 50.67 mm | 43.46 mm |
| Diameter at Shoulder, mm | 21.54 mm | 25.74 mm |
| Diameter at Midpoint, mm | 17.92 mm | 20.25 mm |
| Amount exposed (above ground): none, 1-10%, 11-20%, 21-30%, 31-40%, >40% | None | None |
| Shape: round, conic, cylindrical | Cylindrical | Cylindrical |
| Collar: Sunken, level, square | Level | Level |
| Shoulder: rounded, sloping, square | Rounded | Rounded |
| Base: Pointed, medium, blunt | Pointed | Pointed |
| Surface Smoothness: very smooth, dimpled or corrugated | Very smooth | Very smooth to dimpled |
| Number of Secondary Root Scars: none, few, many | Few | Few |
| Appearance of Secondary Root Scars: not prominent, prominent | Prominent | Prominent |
| Halo: None, faint, prominent | Prominent | Prominent |
| Zoning: None, faint, prominent | Prominent | Prominent |
| Below Ground Exterior Shoulder Color: | Dark purple (RHS N187A) | Dark purple (RHS N186A) |
| Below Ground Exterior Skin Color: | Dark purple (RHS N187A) | Dark purple (RHS N186A) |
| X-Section Interior Xylem (Core) Color: | Yellow (RHS 163C) | Yellow (RHS 163D) |
| X-Section Interior Phloem Color: | Light purple (RHS 183A) | Purple (RHS N186B) |

TABLE 2

Characteristics of Carrot Variety NUN 89733 CAC and the Reference Variety (Non-USDA Descriptors)

| Characteristics | Application Variety (NUN 89733 CAC) | Reference Variety (NUN 89731 CAC) |
|---|---|---|
| Plant top (at harvest stage): | | |
| Foliage: width of crown very narrow, very narrow to narrow, narrow, narrow to medium, medium, medium to broad, broad, broad to very broad, very broad | Medium | Medium |
| Leaf (at harvest maturity): | | |
| Attitude: erect, semi-erect, prostrate | Semi-erect | Semi-erect |
| Length including petiole: very short, very short to short, short, short to medium, medium, medium to long, long, long to very long, very long | Short to medium | Medium |
| Length including petiole, cm: | 50.15 cm | 60.92 cm |
| Intensity of green color: very light, very light to light, light, light to medium, medium, medium to dark, dark to very dark, very dark | Medium | Medium |
| Anthocyanin coloration of petiole: absent, present | Absent | Absent |
| Petiole diameter, mm: | 3.98 mm | 6.23 mm |
| Root (at market maturity): | | |
| Ratio of length/width: very small, very small to small, small, small to medium, medium, medium to large, large, large to very large, very large | Large | Large |
| Extend of green color of skin of shoulder: absent or very small, very small to small, small, small to medium, medium, medium to large, large, large to very large, very large | Absent or very small | Absent or very small |
| Shape in longitudinal section: circular, obovate, obtriangular (conical), narrow obtriangular, narrow obtriangular to narrow oblong, narrow oblong | Narrow obtriangular | Narrow obtriangular |
| Varieties between narrow obtriangular and narrow obtriangular: Tendency to conical shape absent or very weak, very weak, very weak to weak, weak, weak to medium, medium, medium to strong, strong, strong to very strong, very strong | Very strong | Very strong |
| Shape of shoulder: flat, flat to rounded, rounded, rounded to conical, conical | Rounded | Rounded |
| Tip (when fully developed): blunt, slightly pointed, strongly pointed | Strongly pointed | Strongly pointed |
| Ridging of surface: absent or very weak, very weak, very weak to weak, weak, weak to medium, medium, medium to strong, strong, strong to very strong, very strong | Absent or very weak | Very weak to weak |

TABLE 2-continued

Characteristics of Carrot Variety NUN 89733 CAC and the Reference Variety (Non-USDA Descriptors)

| Characteristics | Application Variety (NUN 89733 CAC) | Reference Variety (NUN 89731 CAC) |
|---|---|---|
| Extent of green coloration of interior in longitudinal section: absent or very small, very small to small, small, small to medium, medium, medium to large, large, large to very large, very large | Absent or very small | Small |
| Root weight (g): | 58.87 g | 73.2 g |
| Colors: | | |
| Excluding varieties with white core: intensity of color of core: | Medium | Light to medium |
| Excluding varieties with white core: intensity of color of cortex: | Light | Medium |
| Color of core compared to color of cortex: | Lighter | Lighter |
| Intensity of external color: | Dark | Medium to dark |

TABLE 3

Distinguishing Characteristics between Carrot Variety NUN 89733 CAC and the Reference Variety

| Characteristics | Application Variety (NUN 89733 CAC) | Reference Variety (NUN 89731 CAC) |
|---|---|---|
| Plant Top (at harvest stage): | | |
| Habit: erect, semi-erect, prostrate | Semi-erect | Semi-erect to prostrate |
| Plant Top Height (from Shoulder to Top of Crown), cm | 19.80 cm | 25.57 cm |
| Leaf (at harvest stage): | | |
| Blade division: fine, medium, coarse | Medium | Medium to coarse |
| Blade Length (Without Petiole), cm | 19.69 cm | 28.28 cm |
| Petiole Pubescence: absent, present | Absent | Present |
| Length including petiole: very short, very short to short, short, short to medium, medium, medium to long, long, long to very long, very long | Short to medium | Medium |
| Petiole diameter, mm: | 3.98 mm | 6.23 mm |
| Root (at market maturity): | | |
| Core (Xylem) Thickness (Midpoint X-Section), mm | 8.33 mm | 10.36 mm |
| Carrot Length (Minus Taproot), cm | 22.92 cm | 24.95 cm |
| Length of Taproot, mm | 50.67 mm | 43.46 mm |
| Diameter at Shoulder, mm | 21.5 mm | 25.74 mm |
| Diameter at Midpoint, mm | 17.92 mm | 20.25 mm |
| Surface Smoothness: very smooth, dimpled or corrugated | Very smooth | Very smooth to dimpled |
| Ridging of surface: absent or very weak, very weak, very weak to weak, weak, weak to medium, medium, medium to strong, strong, strong to very strong, very strong | Absent or very weak | Very weak to weak |
| Extent of green coloration of interior in longitudinal section: absent or very small, very small to small, small, small to medium, medium, medium to large, large, large to very large, very large | Absent or very small | Small |
| Root weight (g): | 58.87 g | 73.2 g |
| Colors: | | |
| Below Ground Exterior Shoulder Color: | Dark purple (RHS N187A) | Dark purple (RHS N186A) |
| Below Ground Exterior Skin Color: | Dark purple (RHS N187A) | Dark purple (RHS N186A) |
| X-Section Interior Xylem (Core) Color: | Yellow (RHS 163C) | Yellow (RHS 163D) |
| X-Section Interior Phloem Color: | Light purple (RHS 183A) | Purple (RHS N186B) |
| Excluding varieties with white core: intensity of color of core: | Medium | Light to medium |
| Excluding varieties with white core: intensity of color of cortex: | Light | Medium |
| Intensity of external color: | Dark | Medium to dark |

The results of the T-test show significant differences at 5% significance level between carrot variety NUN 89733 CAC and the Reference Variety for plant top height, blade length without petiole, petiole diameter, core (xylem) thickness, carrot length minus taproot, taproot length, root diameter at shoulder, root diameter at midpoint, and root weight as shown in Tables 4-12.

Table 4 shows a significant difference between carrot variety NUN 89733 CAC and the Reference Variety ($p<0.001$) for plant top height (cm) based on the results of the trial conducted in the US during the trial season 2020.

TABLE 4

| Statistical Parameters | Application Variety (NUN 89733 CAC) | Reference Variety (NUN 89731 CAC) |
|---|---|---|
| Number of samples | 15 | 15 |
| Min. | 18.0 | 23.50 |
| Max. | 21.50 | 29.50 |
| Median | 20.0 | 25.50 |
| Mean | 19.80 | 25.57 |
| Standard deviation | 0.84 | 1.51 |

Table 5 shows a significant difference between carrot variety NUN 89733 CAC and the Reference Variety ($p<0.001$) for blade length without petiole (cm) based on the results of the trial conducted in the US during the trial season 2020.

TABLE 5

| Statistical Parameters | Application Variety (NUN 89733 CAC) | Reference Variety (NUN 89731 CAC) |
|---|---|---|
| Number of samples | 15 | 15 |
| Min. | 16.10 | 24.90 |
| Max. | 27.80 | 32.70 |
| Median | 28.50 | 27.20 |
| Mean | 19.69 | 28.28 |
| Standard deviation | 3.24 | 2.67 |

Table 6 shows a significant difference between carrot variety NUN 89733 CAC and the Reference Variety ($p<0.001$) for petiole diameter (mm) based on the results of the trial conducted in the US during the trial season 2020.

TABLE 6

| Statistical Parameters | Application Variety (NUN 89733 CAC) | Reference Variety (NUN 89731 CAC) |
| --- | --- | --- |
| Number of samples | 15 | 15 |
| Min. | 3.12 | 4.37 |
| Max. | 5.65 | 8.23 |
| Median | 3.94 | 5.99 |
| Mean | 3.98 | 6.23 |
| Standard deviation | 0.65 | 1.18 |

Table 7 shows a significant difference between carrot variety NUN 89733 CAC and the Reference Variety ($p<0.001$) for core (xylem) thickness based on the results of the trial conducted in the US during the trial season 2020.

TABLE 7

| Statistical Parameters | Application Variety (NUN 89733 CAC) | Reference Variety (NUN 89731 CAC) |
| --- | --- | --- |
| Number of samples | 15 | 15 |
| Min. | 4.51 | 4.36 |
| Max. | 6.0 | 7.46 |
| Median | 5.08 | 5.47 |
| Mean | 5.18 | 5.58 |
| Standard deviation | 0.36 | 0.80 |

Table 8 shows a significant difference between carrot variety NUN 89733 CAC and the Reference Variety ($p=0.005$) for carrot length minus taproot (cm) based on the results of the trial conducted in the US during the trial season 2020.

TABLE 8

| Statistical Parameters | Application Variety (NUN 89733 CAC) | Reference Variety (NUN 89731 CAC) |
| --- | --- | --- |
| Number of samples | 15 | 15 |
| Min. | 19.70 | 22.60 |
| Max. | 26.0 | 28.90 |
| Median | 22.80 | 24.70 |
| Mean | 22.92 | 24.95 |
| Standard deviation | 1.89 | 1.74 |

Table 9 shows a significant difference between carrot variety NUN 89733 CAC and the Reference Variety ($p=0.006$) for taproot length (mm) based on the results of the trial conducted in the US during the trial season 2020.

TABLE 9

| Statistical Parameters | Application Variety (NUN 89733 CAC) | Reference Variety (NUN 89731 CAC) |
| --- | --- | --- |
| Number of samples | 15 | 15 |
| Min. | 40.20 | 30.07 |
| Max. | 57.71 | 60.93 |
| Median | 51.26 | 42.85 |
| Mean | 50.67 | 43.46 |
| Standard deviation | 5.11 | 7.98 |

Table 10 shows a significant difference between carrot variety NUN 89733 CAC and the Reference Variety ($p<0.001$) for root diameter at shoulder (mm) based on the results of the trial conducted in the US during the trial season 2020.

TABLE 10

| Statistical Parameters | Application Variety (NUN 89733 CAC) | Reference Variety (NUN 89731 CAC) |
| --- | --- | --- |
| Number of samples | 15 | 15 |
| Min. | 19.13 | 21.82 |
| Max. | 25.47 | 30.59 |
| Median | 21.24 | 25.64 |
| Mean | 21.54 | 25.74 |
| Standard deviation | 1.78 | 2.69 |

Table 11 shows a significant difference between carrot variety NUN 89733 CAC and the Reference Variety ($p<0.001$) for root diameter at midpoint (mm) based on the results of the trial conducted in the US during the trial season 2020.

TABLE 11

| Statistical Parameters | Application Variety (NUN 89733 CAC) | Reference Variety (NUN 89731 CAC) |
| --- | --- | --- |
| Number of samples | 15 | 15 |
| Min. | 15.45 | 17.88 |
| Max. | 19.57 | 22.04 |
| Median | 17.92 | 20.11 |
| Mean | 17.92 | 20.25 |
| Standard deviation | 1.31 | 1.01 |

Table 12 shows a significant difference between carrot variety NUN 89733 CAC and the Reference Variety ($p=0.010$) for root weight (g) based on the results of the trial conducted in the US during the trial season 2020.

TABLE 12

| Statistical Parameters | Application Variety (NUN 89733 CAC) | Reference Variety (NUN 89731 CAC) |
| --- | --- | --- |
| Number of samples | 15 | 15 |
| Min. | 42.0 | 50.0 |
| Max. | 82.0 | 106.0 |
| Median | 52.0 | 72.0 |
| Mean | 56.87 | 73.20 |
| Standard deviation | 14.01 | 18.15 |

The results of the T-test show no significant differences at 5% significance level between carrot variety NUN 89733 CAC and the Reference Variety for plant top neck diameter, petiole length from crown to first pinna, and core (phloem) thickness as shown in Tables 13-15.

Table 13 shows no significant difference between carrot variety NUN 89733 CAC and the Reference Variety ($p=0.717$) for plant top neck diameter (mm) based on the results of the trial conducted in the US during the trial season 2020.

TABLE 13

| Statistical Parameters | Application Variety (NUN 89733 CAC) | Reference Variety (NUN 89731 CAC) |
| --- | --- | --- |
| Number of samples | 15 | 15 |
| Min. | 7.91 | 10.35 |
| Max. | 21.72 | 13.85 |
| Median | 11.61 | 12.14 |
| Mean | 11.90 | 12.22 |
| Standard deviation | 3.18 | 0.97 |

Table 14 shows no significant difference between carrot variety NUN 89733 CAC and the Reference Variety (p=0.162) for petiole length from crown to first pinna (cm) based on the results of the trial conducted in the US during the trial season 2020.

TABLE 14

| Statistical Parameters | Application Variety (NUN 89733 CAC) | Reference Variety (NUN 89731 CAC) |
|---|---|---|
| Number of samples | 15 | 15 |
| Min. | 25.30 | 24.80 |
| Max. | 34.90 | 44.60 |
| Median | 30.90 | 32.90 |
| Mean | 30.47 | 32.64 |
| Standard deviation | 3.10 | 4.97 |

Table 15 shows no significant difference between carrot variety NUN 89733 CAC and the Reference Variety (p=0.089) for cortex (phloem) thickness based on the results of the trial conducted in the US during the trial season 2020.

TABLE 15

| Statistical Parameters | Application Variety (NUN 89733 CAC) | Reference Variety (NUN 89731 CAC) |
|---|---|---|
| Number of samples | 15 | 15 |
| Min. | 4.51 | 4.36 |
| Max. | 6.0 | 7.46 |
| Median | 5.08 | 5.47 |
| Mean | 5.18 | 5.58 |
| Standard deviation | 0.36 | 0.80 |

The invention claimed is:

1. A plant, plant part, or seed of variety NUN 89733 CAC, or regenerable part thereof, wherein a representative sample of seed of said carrot variety NUN 89733 CAC is deposited under Accession Number NCIMB 44118.

2. A plant part of claim 1, wherein the plant part is a leaf, pollen, an ovule, a fruit, a root, a taproot, cutting, a flower, or a cell.

3. The plant part of claim 1, wherein the plant part is a root.

4. A plant or regenerable part thereof, produced by growing the seed of carrot variety NUN 89733 CAC, wherein a representative sample of seed of said carrot variety NUN 89733 CAC is deposited under Accession Number NCIMB 44118.

5. A carrot plant or a part thereof having all of the physiological and morphological characteristics of the carrot plant of claim 1, when grown under the same environmental conditions.

6. A tissue or cell culture of regenerable cells of the plant or plant part of claim 1.

7. The tissue or cell culture according to claim 6, comprising cells or protoplasts obtained from a plant part suitable for vegetative reproduction, wherein the plant part is a meristem, a cotyledon, a hypocotyl, a seed coat, a leaf, an anther, a root, a root tip, a taproot, a pistil, a petiole, a flower, a fruit, a stem, or a stalk.

8. A carrot plant regenerated from the tissue or cell culture of claim 6, wherein the plant has all of the physiological and morphological characteristics of carrot variety NUN 89733 CAC, when the numerical characteristics are determined at the 5% significance level and determined by type or degree for non-numerical characteristics for plants grown under the same environmental conditions, and wherein a representative sample of seed of said carrot variety has been deposited under Accession Number NCIMB 44118.

9. A method of producing the plant of claim 1 or a part thereof, said method comprising vegetative propagation of at least a part of the plant of carrot variety NUN 89733 CAC.

10. The method of claim 9, wherein said vegetative propagation comprises regenerating a whole plant from said part of carrot variety NUN 89733 CAC, wherein a representative sample of seed of said carrot variety has been deposited under Accession Number NCIMB 44118.

11. The method of claim 9, wherein said part is a cutting, a cell culture, or a tissue culture.

12. A vegetative propagated plant of claim 1, wherein the vegetative propagated plant has all of the physiological and morphological characteristics of carrot variety NUN 89733 CAC, when the numerical characteristics are determined at the 5% significance level and determined by type or degree for non-numerical characteristics for plants grown under the same environmental conditions, and wherein a representative sample of seed of said carrot variety has been deposited under Accession Number NCIMB 44118.

13. A method of producing a carrot plant, said method comprising crossing the plant of claim 1 with a second carrot plant at least once, and selecting a progeny carrot plant from said crossing and optionally allowing the progeny to form seed, and wherein a representative sample of seed of carrot variety NUN 89733 CAC has been deposited under Accession Number NCIMB 44118.

14. A method of producing a carrot plant, said method comprising crossing carrot plants and harvesting the resultant seed, wherein at least one carrot plant in the cross is the plant of claim 1, wherein a representative sample of seed of said carrot variety has been deposited under Accession Number NCIMB 44118.

15. A carrot plant having one physiological or morphological characteristic which is different from those of the plant of claim 1, and which otherwise has all the physiological and morphological characteristics of the plant of carrot variety NUN 89733 CAC, when the numerical characteristics are determined at the 5% significance level and determined by type or degree for non-numerical characteristics for plants grown under the same environmental conditions, and wherein a representative sample of seed of said carrot variety has been deposited under Accession Number NCIMB 44118, wherein said different characteristics is conferred by a transgene.

16. A method of producing doubled haploids of the plant of claim 1, said method comprising making doubled haploid cells from haploid cells made from the plant or regenerable part thereof of claim 1 by chromosome doubling, and wherein a representative sample of seed of said carrot variety has been deposited under Accession Number NCIMB 44118.

17. A method of producing a carrot root, said method comprising obtaining the plant according to claim 1, wherein the plant has been cultivated to maturity, and collecting the root from the plant.

18. A carrot root produced by the method of claim 17.

19. A container comprising the carrot root collected in the method of claim 17.

20. A container comprising the plant part of claim 3.

21. A container comprising the seed of claim 1.

22. A food or a feed product comprising the carrot root, or parts thereof, of claim 5.

23. A method of introducing a desired trait into the plant of claim 1, said method comprising transforming the plant of carrot variety NUN 89733 CAC with a transgene that confers the desired trait, wherein the desired trait is male sterility, herbicide tolerance, insect resistance, pest resistance, disease resistance, environmental stress tolerance, modified carbohydrate metabolism, or modified protein metabolism.

24. A carrot plant produced by the method of claim 23, wherein the plant comprises the desired trait and otherwise all of the physiological and morphological characteristics of carrot variety NUN 89733 CAC.

25. A method of producing a modified carrot plant, said method comprising mutating the plant of carrot variety NUN 89733 CAC and selecting a mutated plant with the desired trait, wherein a representative sample of seed of said carrot variety has been deposited under Accession Number NCIMB 44118.

26. A method for determining the genotype of the plant of claim 1, said method comprising obtaining a sample of nucleic acids from said plant and detecting in said nucleic acid a plurality of polymorphisms, thereby determining the genotype of the plant and storing the results of detecting the plurality of polymorphisms on a computer readable medium.

27. A method of producing a carrot plant derived from the plant of claim 1, comprising:
  a. preparing a progeny carrot plant derived from carrot variety NUN 89733 CAC by crossing the plant of any of claim 1 with itself or with a second carrot plant, wherein a representative sample of seed of said carrot variety has been deposited under Accession Number NCIMB 44118;
  b. crossing the progeny plant with itself or a second carrot plant to produce seed of a progeny plant of a subsequent generation;
  c. growing a progeny plant of a subsequent generation from said seed and crossing the progeny plant of a subsequent generation with itself or a second carrot plant;
  d. repeating steps (b) and/or (c) for at least one more generation to produce a carrot plant derived from carrot variety NUN 89733 CAC.

* * * * *